United States Patent [19]

Wernikoff

[11] 4,382,184

[45] May 3, 1983

[54] APPARATUS AND METHOD FOR SIMULTANEOUSLY DISPLAYING RELATIVE DISPLACEMENTS OF A FLUCTUATING BIOLOGICAL OBJECT

[75] Inventor: Robert E. Wernikoff, Boston, Mass.

[73] Assignee: Cardiac Imaging Limited Partnership, Westport, Conn.

[21] Appl. No.: 963,373

[22] Filed: Nov. 24, 1978

[51] Int. Cl.[3] ............... G03B 41/16; H05G 1/30; G01T 1/00
[52] U.S. Cl. .................... 378/37; 128/653; 250/505.1; 378/62; 378/96; 378/99; 378/165; 378/155
[58] Field of Search ........ 250/413, 402, 322, 416 TV, 250/509, 323, 320, 313, 314, 355, 363 S, 505, 401, 476; 354/110, 120, 124, 125; 128/653, 659, 661, 664, 671, 668, 708

[56] References Cited

U.S. PATENT DOCUMENTS

| | | | |
|---|---|---|---|
| 1,478,278 | 12/1923 | Harlow | 354/125 |
| 1,482,070 | 1/1924 | Douglass | 354/110 |
| 1,704,974 | 3/1929 | Katzman | 250/471 |
| 1,858,661 | 5/1932 | Decker | 354/125 |
| 2,190,389 | 2/1940 | Strauss et al. | 250/413 |
| 2,747,104 | 5/1956 | Jacobs | 250/401 |
| 3,605,724 | 9/1971 | Flaherty | 128/661 |
| 3,626,932 | 12/1971 | Becker | 250/402 |
| 3,825,761 | 7/1974 | Geratsdorfer | 250/402 |
| 3,871,360 | 3/1975 | Van Horn et al. | 128/671 |

FOREIGN PATENT DOCUMENTS

| | | | |
|---|---|---|---|
| 490299 | 2/1937 | United Kingdom | 250/452 |
| 143508 | 4/1961 | U.S.S.R. | 250/320 |

*Primary Examiner*—Alfred E. Smith
*Assistant Examiner*—Carolyn E. Fields
*Attorney, Agent, or Firm*—Epstein & Edell

[57] ABSTRACT

X-ray apparatus and method for producing discrete images of a human organ in fluctuating motion, e.g., the heart and related vessels. Each image is derived at a selected time related to the cardiac cycle. The images are independently presented on respective discrete areas within a common image plane. A source of X-rays irradiates the organ. A physiological synchronizer produces timing signals within the cardiac cycle for controlling the periods of transmission of the X-ray beam through the organ during, for example, end diastole and end systole. An antiscattering, masking frame has alternate parallel slits and bars at equal intervals exposing substantially half the area of presentation of an X-ray sensitive film in alternate, equally spaced area strips during, e.g., diastole. The frame is repositioned in response to a signal from the synchronizer for actuating it relative to the film such that the bars then cover the sensitized areas of the film and expose substantially the remaining half of the film during systole. The image elements are interdigitally juxtaposed to present the diastolic and systolic images in an interlaced pattern. Relative displacements of the organ during a cardiac cycle may be determined from the juxtaposed image elements.

40 Claims, 30 Drawing Figures

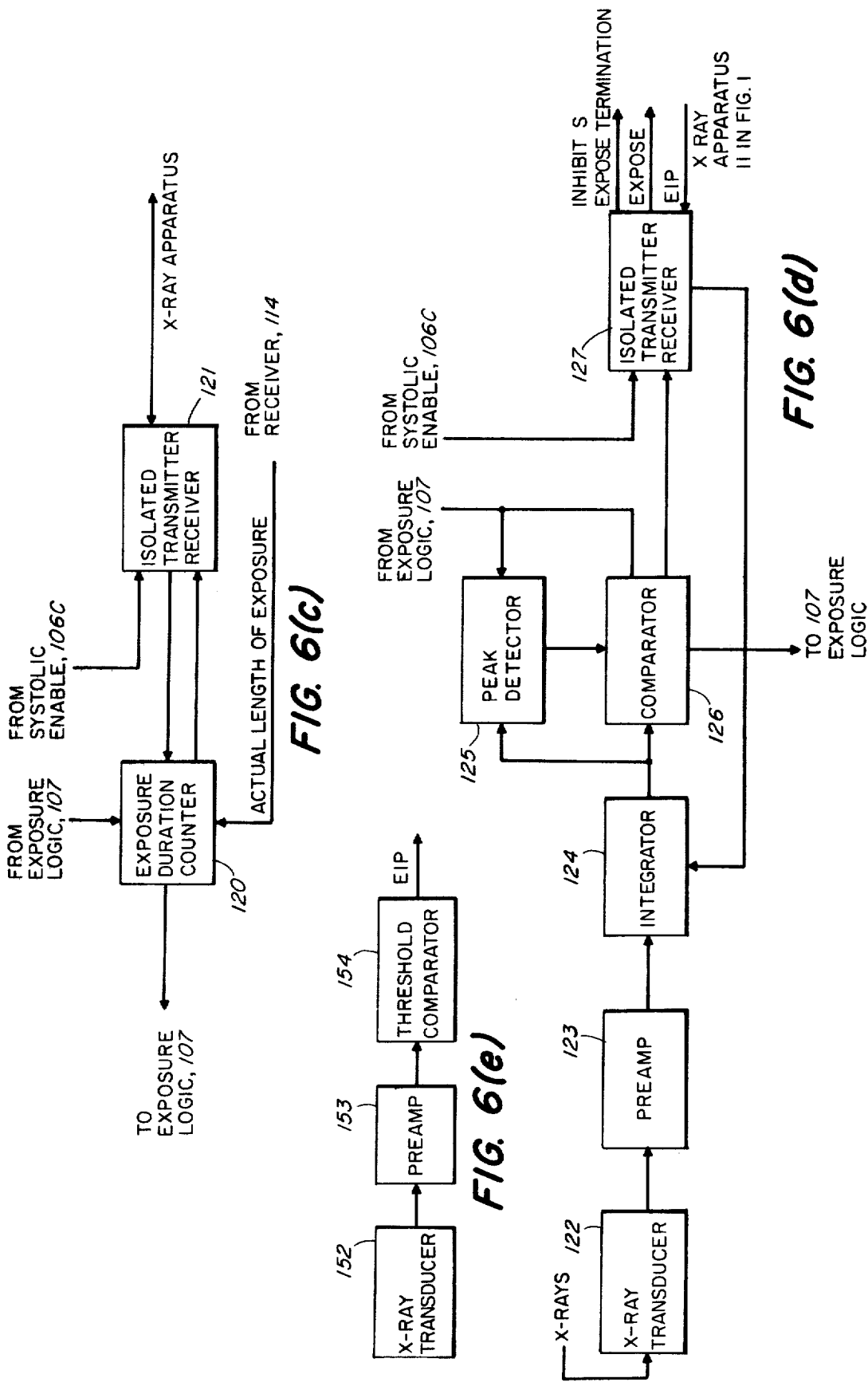

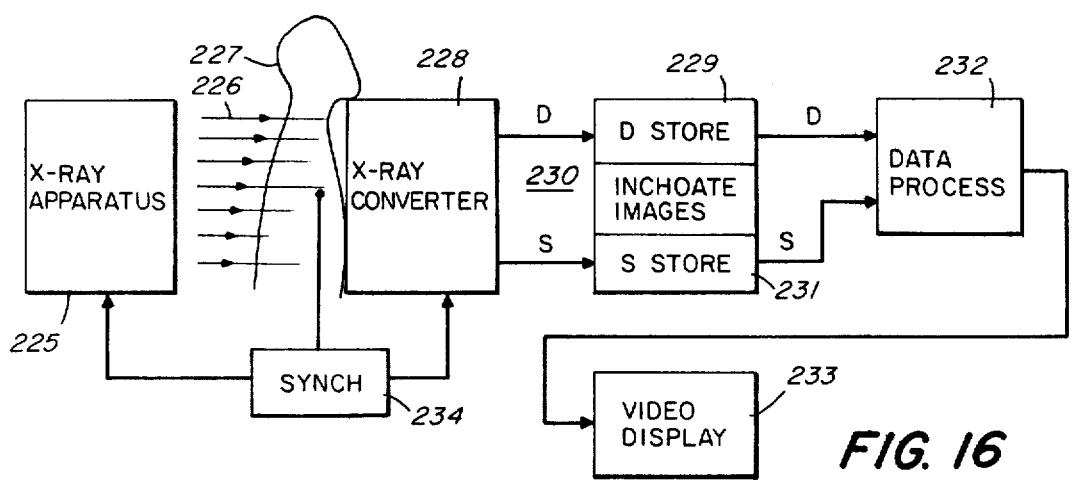
FIG. 16
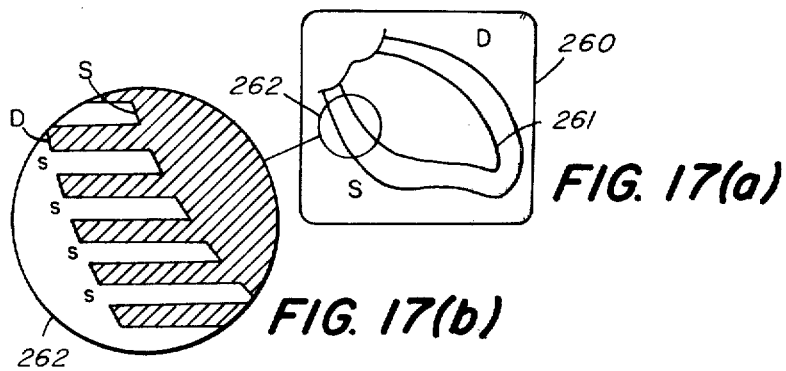
FIG. 17(a)
FIG. 17(b)
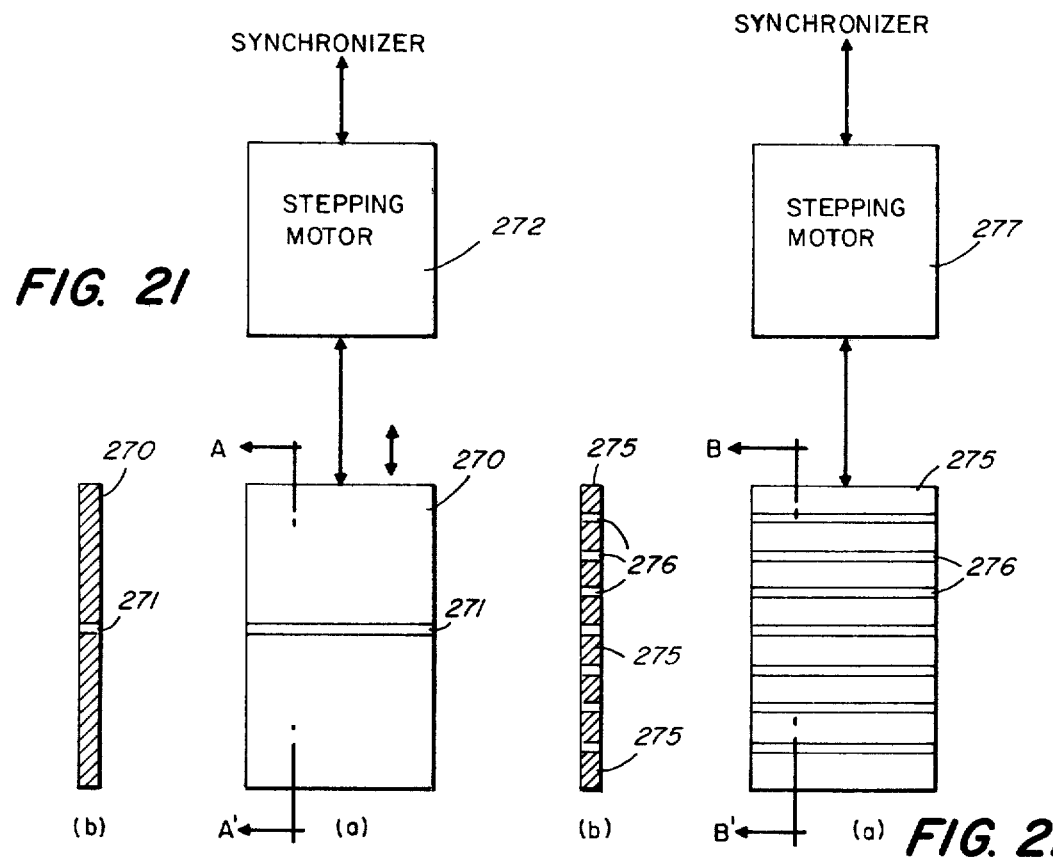
FIG. 21
FIG. 22

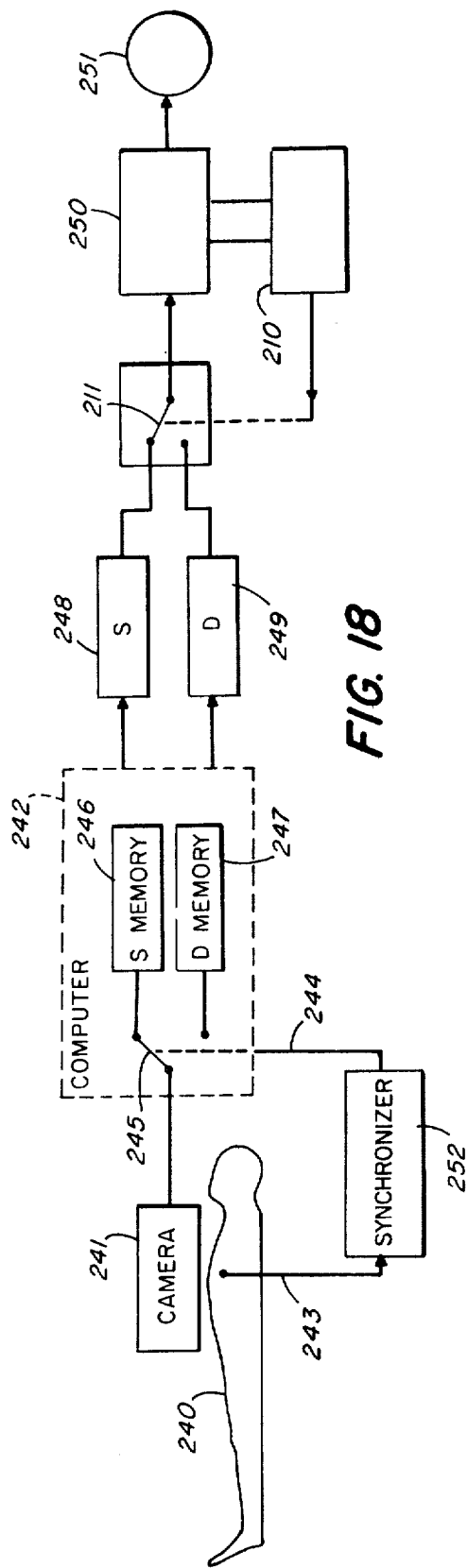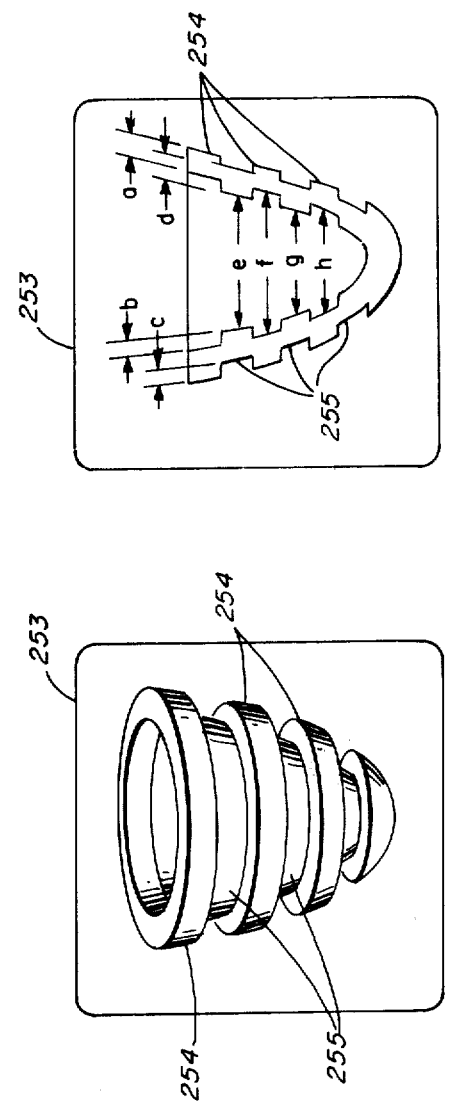
FIG. 18
FIG. 19
FIG. 20

APPARATUS AND METHOD FOR SIMULTANEOUSLY DISPLAYING RELATIVE DISPLACEMENTS OF A FLUCTUATING BIOLOGICAL OBJECT

BACKGROUND OF THE INVENTION

1. Field of the Invention

The invention relates generally to the field of viewing a biological object by irradiation to expose the internal structure. More particularly, the invention relates to diagnosis of human ailments by the use of X-ray or nuclear radiation as modified to view specific organs, and associated vessels, while in fluctuation, whether or not recurrent, and to exposures taken during fluctuation at selected times related to a selected physiological state or states of the object.

More especially, the present invention relates to producing a radiograph for simultaneously, statically viewing the heart and associated vessels, after exposure to radiation, at different times in the cardiac cycle, for example, during systole and diastole respectively.

2. Conventional X-Radiological Diagnosis

X-radiology is widely used noninvasively, that is, without invading the body by puncture or chemical agents, as part of routine health examinations and preliminary tests where pathology may be indicated. Where indicated clinically, the use of invasive, risky and complex arteriography or angiography is becoming more frequent.

Chest X-Ray

In modern X-radiology, for example, for a chest X-radiograph, an X-ray tube provides a source of X-radiation to illuminate a patient's chest. The X-radiation from the patient is transmitted through X-radiation sensitive film, normally enhanced by X-radiation transmitted through a fluorescent light screen positioned behind the film. The fluorescent screen is required because the film is more sensitive to light than to X-rays. Generally speaking, the X-ray tube anode voltage is approximately 70 kilovolts. The exposure time required for a useful X-radiograph is typically in the range of 50-100 milliseconds. The exposure is initiated by applying the anode voltage to the tube, and it is extinguished by removing the voltage.

The operator selects the amount of X-radiation exposure by means of (1) a calibrated timing mechanism for the period of an exposure or (2) a calibrated phototimer for counting and summing X-rays or photons, to control the application of anode voltage. The so-called phototimer typically employs a photomultiplier tube and integrating circuit to control the exposure in terms of a preselected photon count. To provide a proper radiograph for ready analysis, the exposure is so chosen as to provide an image varying in density with a maximum visible range for detecting variations in skeletal and tissue structure. Further, maximum contrast is considered desirable to enhance structural details.

The apparent fine detail is further enhanced by minimizing undesirable, so-called scattered, radiation; that is, nonparallel or uncollimated X-rays. In a typical X-radiographic film a screening, or anti-scattering, web is used in front of the film to reduce the scattering by restricting exposure substantially to parallel rays. Mechanisms for reducing such scattering are fully described in the literature; and, particularly, reference is made to an article entitled "Radiographic Contrast Improvement by Means of Slit Radiography" by Jaffe et al appearing in Radiology Vol. 116, pages 631-635, September 1975.

The resultant X-radiographic image obtained is derived from direct X-radiation and indirectly from the light from the fluorescent screen, produced in accordance with the photoelectric effect by X-radiation impinging upon fluorescent materials.

A minimal effort is made to control the patient exposure to radiation to normalize one radiographic image relative to another. More particularly with regard to specific physiological states, it is not currently widely considered important to synchronize the X-ray exposure with any particular physiological state. Nor is it considered important, in a precise manner, to normalize the radiograph in other respects, such as density and contrast. Thus, if one is taking a normal chest X-ray, the exposure can take place during a period when the fluctuations or displacements of any organ, particularly the heart, are most rapid. This has the effect of obscuring or blurring the image, particularly the outlines. Consequently, incipient calcification, for example, frequently fails to show up without such synchronization. Such radiographic images may be, in part, totally obscured; at the very least much of the image is extremely difficult to interpret.

In any event, the normal or conventional chest X-ray gives one no indication of what happens dynamically, when the heart is in motion. The time during the cardiac cycle when the exposure takes place is unknown; that is, the exposure is taken without relation to the heart motion. In addition relative displacements or changes in condition are not shown.

Angiography

At this time angiography has proven to be the most reliable procedure for diagnosing cardiovascular pathology because the heart motion and blood flow may be viewed dynamically. This risky, complex and invasive technique requires the insertion of a catheter through the main artery, the aorta, to inject a dye into the arteries feeding the heart, the coronary arteries. A large number of X-radiographs are taken sequentially and edited to provide, by time-lapsed radiography, a radiographic motion picture depicting the amplitude and character of heart fluctuation and blood flow during the cardiac cycle.

Angiography requires a highly trained team. The necessary time involving the patient ranges from 2-6 hours and, indeed, must occasionally be repeated. Ideally angiography should be repeated after surgery to establish the efficacy of the surgery.

This technique impacts heavily on the patient requiring a high level of cooperation. The patient is immobilized during the entire procedure, supported only on a hard, flat surface.

3. Problems with Conventional Techniques

Static X-Radiographs

The procedure widely accepted, at this time, as standard X-radiology for routine examinations and preliminary testing is inadequate because:

1. The radiographic image tends to blur if the exposure is taken at random; that is, unsynchronized with the time of minimum motion of the heart; and
2. No information is presented as to the relative displacements of the heart during the cardiac cycle.

Disadvantages of Angiography

Angiography in its present form is limited in use to an indication of severe heart disease because:
1. It is dangerous. The risk of a catastrophe at the best facilities in 1976 was 1%, with a 0.5% mortality rate. In lesser facilities the catastrophe rate was much higher;
2. A large team of highly trained specialists is required;
3. The procedure is lengthy, complex and expensive;
4. It is difficult and sometimes impossible to apply to comatose patients;
5. The X-radiation exposure time is enormous with typical 50-150 milliseconds for standard chest X-ray; and
6. The patient is subjected to a high level of discomfort and debilitation.

In 1976 about 70,000,000 chest X-rays alone were taken and less than 50,000 angiographs. If every patient who requires angiography were so diagnosed, existing facilities would be severely overtaxed. Clearly neither the presently accepted standard or angiographic radiological procedures are adequate as a routine diagnostic tool for cardiovascular disorders, let alone all other disorders requiring X-radiological diagnostic procedures.

4. What Is Needed?

Broadly, an X-radiological diagnostic technique is objectively needed as convenient as the standard, routine procedure and providing as much, or more, information of diagnostic interest as angiography. At the moment, an intermediate solution, as close as possible to the ideal objective described above, would be enormously important for:
1. Screening candidates for angiography and other complex procedures;
2. Increasing the validity of stress tests; and
3. Increasing the validity of diagnosis for routine health examinations and preliminary tests.

More particularly, there is a clear and present need for an X-radiological, diagnostic procedure which:
1. Is not invasive;
2. Minimizes patient exposure to radiation;
3. Is compatible with current standard practice for routine radiography;
4. Presents more useful diagnostic information without substantially degrading the current radiographic image. In providing information as to heart motion, for example, the lung tissue structure must be undisturbed;
5. Is compatible with readily retrofitting existing installations;
6. Has minimum impact on the number and training of personnel required for performing the radiography;
7. Has minimum impact on the time, precision and equipment necessary;
8. Is relatively inexpensive; and
9. Presents information, for example, with respect to pulsation amplitudes of an organ in such a manner as to be readily assimilated by eye, clearly and unambiguously.

5. Disadvantages of Prior Art Solutions to the Conventional Problems

The need for observing X-radiographs of the heart in motion to observe relative displacement has long been recognized. A technique commonly referred to as kymography has been the subject of extensive experimentation since 1911 for use in cardiovascular diagnosis.

More recently the need for synchronizing X-radiation exposures with selected physiological states is well known. More particularly the use of a physiological synchronizer to synchronize radiation exposure with minimum motion during, for example, the cardiac cycle is well understood.

Kymography

Kymography is widely described in the literature and particularly summarized recently in a book entitled "The Heart and It's Action: Roentgenkymographic Studies", by Dr. Gilbert H. Alexander, published 1970 by Warren H. Green, St. Louis, Missouri.

In the preferred mode as described by Alexander, a patient is continuously X-irradiated for periods in excess of 1.5 seconds. A horizontal slit in a curtain shutter, similar to the well-known focal plane camera shutter and positioned between the patient and the image plane, continuously moves vertically downward to expose X-ray film continuously to depict the cardiac image as it fluctuates during the cardiac cycle. The resultant kymograph reveals a wavelike, or kyma, effect in the heart outlines.

The slit width is chosen to be as narrow as possible consistent with other considerations relevant to image quality. The exposure time required is nominally in the range of 40-100 milliseconds. Given a fixed slit width and selected exposure time, the rate of travel of the slit becomes determined. Frequently, three or more cardiac cycles are required, giving rise to patient exposure to radiation greater than 5 seconds, or more. This is 100 times the nominal 50 milliseconds exposure required in current practice.

Disadvantages of Kymography

Kymography is now substantially obsolete. Some of the disadvantages are:
1. Excessive exposure to radiation;
2. Since the heart is in diastole for 70%, or more, of the cardiac cycle and in systole 30% or less, the systolic image, particularly during rapid motion, appears very compressed in the radiograph. The systolic image, therefore, appears blurred and ambiguous as to structure;
3. The kymograph is not synchronized with the electrocardiographic signal, thereby leading to an uncertainty as to which parts of the image reveal known displacements of the heart relative to the cardiac cycle;
4. Since the slit motion is continuous, the slit width, exposure time and rate of slit motion are interdependent and, hence, constrained; and
5. Precise measurements of displacements during the cardiac cycle are difficult to make, particularly between extreme positions.

Physiological Synchronizing and Comparison

For the purpose of synchronizing exposures to minimum motion of the heart, physiological synchronizers are typically used for nuclear medicine in cardiology. Since radioactive tracers taken internally are necessarily limited to relatively low levels of radiation, a long exposure of the film, for example 15 minutes, is required during periods of minimum heart motion, such as end systole and end diastole, to obtain a useful image. If the exposure were continuous, the image, of course, would be blurred.

In nuclear medicine as applied to the heart, the source radiation is continuous. A shutter is used to expose the radiation sensitive film within a cardiac cycle only for 50–100 milliseconds each at end systole and/or end diastole, respectively, during minimum heart motion. The resultant image is obtained over a large number of cardiac cycles. Given a nominal 60 beats per minute, an exposure of a nominal 15 minutes implies 900 cardiac cycles to provide a useful image.

The use of synchronized X-radiographs for cardiology has been proposed. One suggestion was proposed by Hipona et al in a journal article entitled "Intercalative Chest Roentgenography", in Radiology, Vol. 82 Pages 304–306, February, 1964. It involves the use of an ECG signal as provided by a physiological synchronizer to produce two X-radiographs, one at end systole and one at end diastole. The resultant radiographs are then compared (1) side by side or (2) superimposed one over the other. This suggestion has not proved useful because of the difficulty in obtaining meaningful information as to relative displacements between systole and diastole. Since the displacements of interest are as low as 1 or 2 millimeters, the measurement can be made only with considerable difficulty. Furthermore, proper registration of the radiographs is exceedingly hard to obtain.

In the latter case, superposition suffers from unacceptable obscuration of image structure in addition to the registration and measurement problems. The suggestion has proved unworkable because it violates the requirement for ready assimilation by eye of the information, clearly and unambiguously. Further, superposition degrades image resolution and violates the criterion of preserving the integrity of the image.

A physiological synchronizer for practising the synchronized comparison method for two separate radiographs, one taken, for example, in systole and the other in diastole, is described and illustrated in U.S. Pat. No. 3,871,360 for "Timing Biological Imaging, Measuring and Therapeutic Systems" issued Mar. 18, 1975, to Van Horn et al and assigned to the present assignee. U.S. Pat. No. 3,871,360 is hereby expressly incorporated herein by reference as an integral part of this specification and disclosure.

An effort to overcome the problems inherent in separate radiographs is described and illustrated in U.S. Pat. No. 3,626,923, issued to Hal C. Becker on Dec. 14, 1971. In Becker's "EKG Synchronized X-Ray Double Pulse Exposure Apparatus and Method" a single X-ray film is double-exposed, one exposure corresponds with end systole, and the other with end diastole. Unfortunately, this approach has not proven useful because of poor resolution. Although there is an improvement in registration, the total exposure represents a net compromise in exposure, tending to degrade the image. The image detail is further degraded by the effect of superposition of the two images; that is, the systolic and diastolic images are not distinct, discrete images. Nevertheless U.S. Pat. No. 3,626,932 is expressly incorporated herein by reference as an integral part of this specification and disclosure.

SUMMARY OF THE INVENTION

In accordance with the preferred mode of the invention, a chest X-radiograph is taken simultaneously presenting two discrete images, each occupying substantially half the area of presentation, one corresponding with end diastole, relaxation or dilation, and the other with end systole, contraction. The exposures are preferably taken within one cardiac cycle during the periods of minimum heart motion in diastole and systole. Thus the diastolic and systolic images are separated in the time domain by a discrete time interval.

Each image is composed of a set of discrete image elements, each element corresponding with an alternating band or discrete area segment. Thus the diastolic image elements are interdigitally presented with the systolic image elements in corresponding indexed area segments. The diastolic and systolic images then appear in an interlaced pattern with each diastolic element in juxtaposition, side by side relation, with a systolic element. In this manner, the systolic and diastolic images are separated in space as well as time, though presented simultaneously in a static radiograph. In the preferred mode, each pair of juxtaposed image elements represents contiguous regions of the irradiated patient. A more complete discussion is presented below with reference to the drawings.

The X-radiograph of the present invention clearly includes all of the advantages of the prior art synchronized-comparison procedures without any of the disadvantages. In particular no substantial degradation of the conventional X-radiographic image takes place because each image element is properly exposed and is discrete. Displacements or other changes in condition are readily perceived by the radiologist because the differences revealed by side by side comparison of image elements are enormously enhanced and the images inherently in excellent registration. Thus, diagnostic information to be defined from the pulsation amplitudes is presented in such a manner as to be readily perceived by eye, clearly and unambiguously.

Heart outlines, for example the left wall of the left ventricle, appear serrated in the radiograph of the invention. These serrations indicate a measure of wall displacement, between, e.g., end diastole and end systole. For image elements about 3 millimeters wide, a standard 14" by 17" radiograph viewed from a distance of 30 feet, the serrations are unexpectedly clear.

1. Definitions

Radiation—the term "radiation" as used herein means all forms of radiation or radiant energy useful in representing an image of a biological object. The term includes all such useful forms of electromagnetic and mechanical radiant energy in all such useful frequencies.

Electromagnetic—the term "electromagnetic" as applied to radiation herein includes, without limitation, radio waves, light and near light, X-rays, nuclear radiation, alpha, beta and gamma particles.

Light—the term "light" as used herein includes all such energy in the frequency range from far infrared to ultraviolet, whether or not visible.

Sound—the terms "sound" or "sonic" as applied to radiation herein includes all mechanical radiant energy in all frequency ranges, whether or not audible.

Photon—the term "photon" as used herein means an elementary discrete bit of electromagnetic radiant energy.

Phonon—the term "phonon" as used herein means an elementary discrete bit of sound energy.

Electrocardiograph—the term "electrocardiograph" as used herein means an instrument for producing an electrocardiac signal, e.g., the well-known QRS complex.

Electrocardiogram—the term "electrocardiogram" as used herein means a tracing of the QRS complex, e.g., as produced by a strip-chart recorder.

Radiograph—the term "radiograph" as used herein means, without limitation, a recorded image derived from image forming radiation.

Fluorescent image—the term "fluorescent image" as used herein means an image derived from fluorescent material.

Inchoate image—the term "inchoate image" as used herein means data from which an image may be displayed or recorded.

2. X-Ray Apparatus

In the preferred mode of the invention, a physiological synchronizer is connected through electrodes to a patient. The synchronizer produces an electrocardiographic signal, ECG signal, in response to the cardiac QRS complex signals from the patient. The synchronizer is coupled to an X-ray apparatus to control the period of irradiation of the patient in accordance with diastolic and systolic timing signals derived from the ECG signal. A masking frame, having parallel fixed bars and slits of equal widths, is interposed between the patient and an X-radiographic film at an image plane, is electromechanically positioned, a distance equal to a slit width, for selectively exposing the film to the diastolic and systolic images by a solenoid. The solenoid is coupled to the synchronizer and actuated by the diastolic and systolic timing signals in synchronism with the patient irradiation.

The X-ray technician initiates the procedure by preselecting the desired amount of exposure and enabling the synchronizer. The patient is X-irradiated in response to the diastolic signal from the synchronizer. The X-radiation from the patient passes through the masking frame which exposes one-half the area of presentation of the film, in alternate bands, to produce a diastolic image. After repositioning the masking frame in such a manner as to mask the previously exposed areas of the film, the remaining half of the presentation is exposed in alternate bands corresponding with a systolic image. The film is then developed to provide the diastolic and systolic images in an interlaced pattern of interdigitally, juxtaposed diastolic and systolic image elements. Each band or area segment is indexed to identify it with respect to diastole and systole.

The images are viewed element by element for evidence of displacement. One may look at the outline, for example, of the wall of the left ventricle. The images thus presented appear serrated, and the distance between the apparent outlines is a measure of the relative displacement of the wall of the left ventricle during the discrete time interval between diastole and systole.

The radiologist can now determine at a glance whether or not the motion of the heart is normal. The evidence to date indicates that normal motion is represented by displacements in the range of 2–4.5 millimeters. Displacement of 5–10 millimeters is considered abnormal at this time.

On the evidence examined to date, the apparent motion observed from radiographs taken in accordance with the invention very strongly correlates with the results of angiography, that is, in excess of 90%. it is noteworthy that the integrity of the lung tissue structure remains substantially intact.

There are a number of occasions when the organ outline in systole crosses over the organ outline in diastole, as in dyskinesis, resulting in an uncertainty as to which outline corresponds with systole or diastole. Because the invention contemplates the use of synchronized, discrete areas, such an ambiguity is precluded by identifying indicia. Thus, in the event of a heart aneurism, a wall outline appears to extend under pressure beyond its position in diastole. For instance, ordinarily the left ventricle contracts during systole and dilates during diastole. An apparent inversion of the wall outlines takes place in the event that there is a significant ventricular aneurism. The apparent ambiguity is easily resolved by referring to the area segment indicia, thereby differentiating diastole from systole.

The apparatus and method, and a discussion of the results of an experiment conducted at Massachusetts General Hospital in Boston, Massachusetts, are described and illustrated in an unpublished article by Dr. Robert E. Dinsmore, Chief of Cardiac Radiology at Massachusetts General Hospital. The article is entitled "The Evaluation of Left Ventricular Free Wall Asynergy due to Coronary Artery Disease: The Use of an Interlaced ECG-Gated Radiographic System" and has been submitted for publication to the American Journal of Roentgentology. The article is hereby incorporated herein as an integral part of this specification and disclosure. A copy of the article is attached to the specification.

DETAILED DESCRIPTION OF THE INVENTION

There follows a detailed description of the preferred embodiments and methods of the invention, taken in connection with the accompanying drawings, and its scope will be pointed out in the appended claims.

IN THE DRAWINGS

Figure 1:
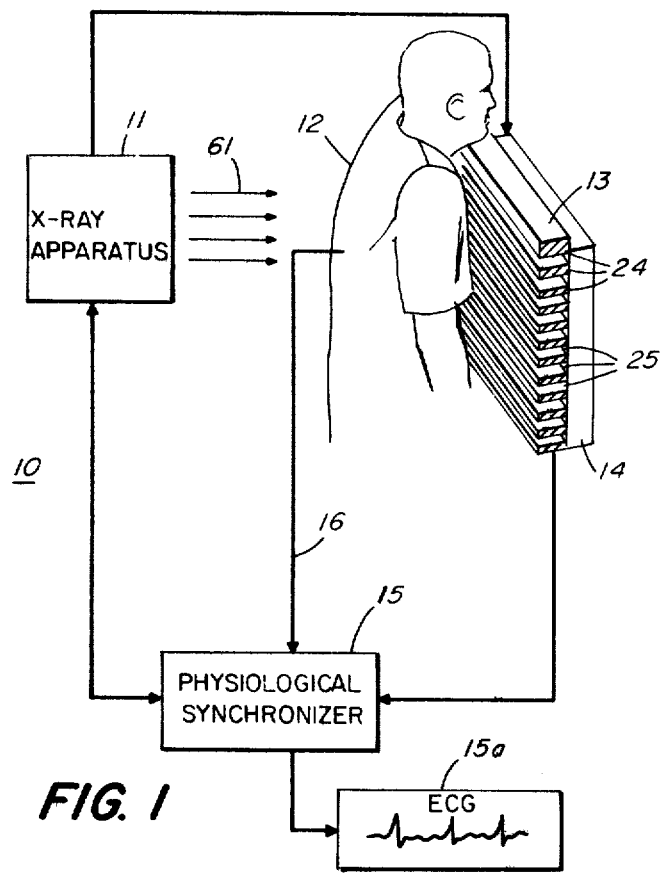
FIG. 1 is a schematic illustration, partially in block diagram, of an X-radiographic system embodying the invention.
Figures 4A, 4B:
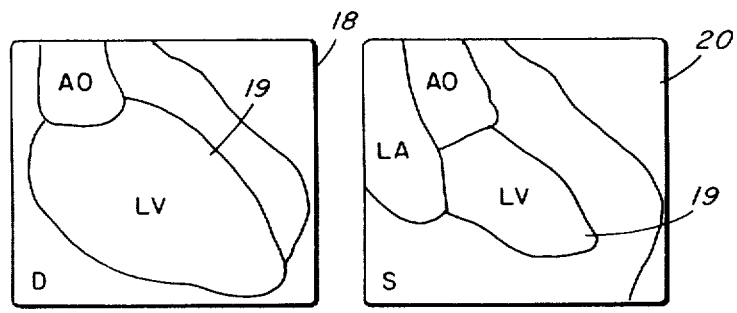
Figure 4C:
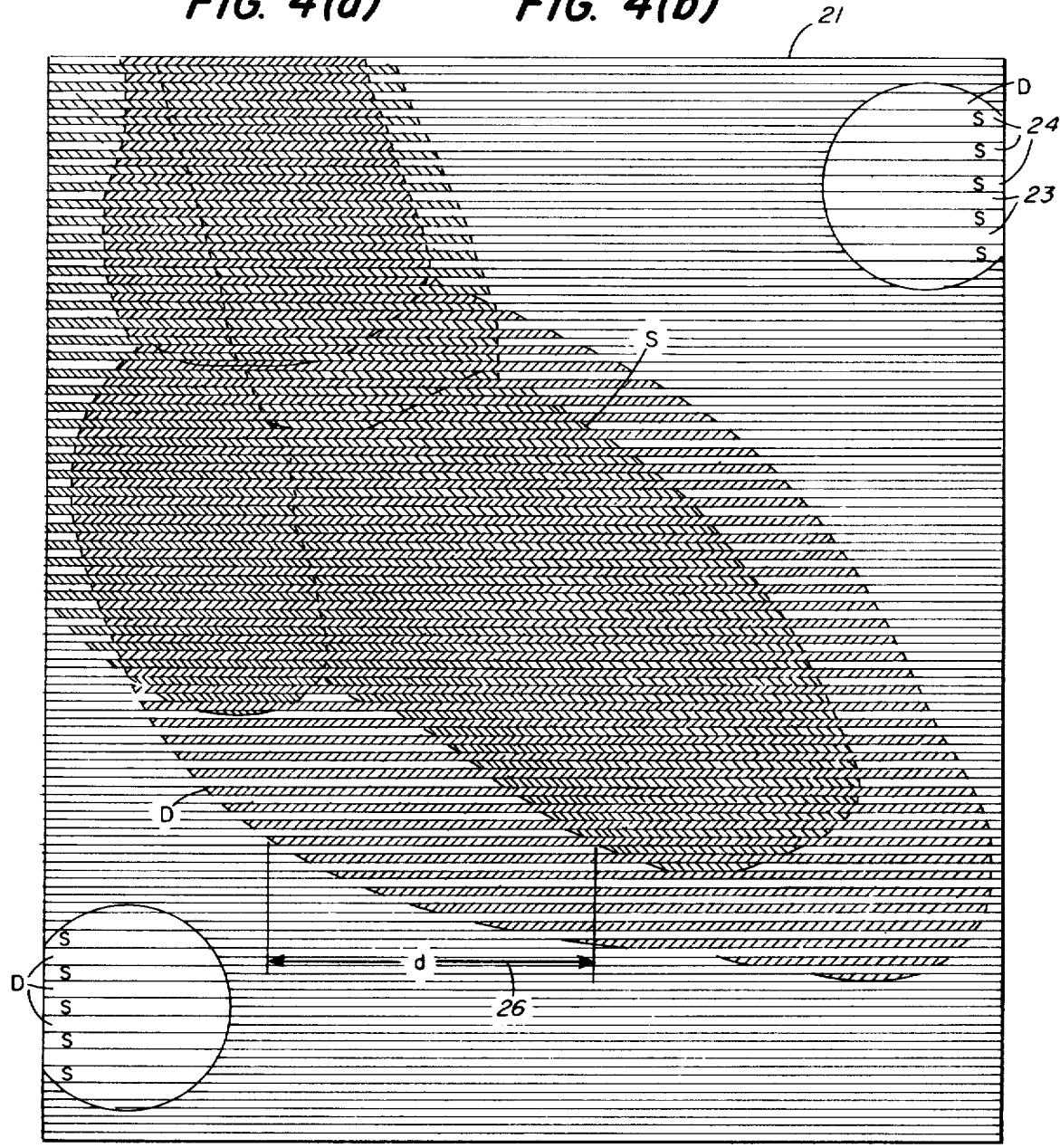
Figure 4D:
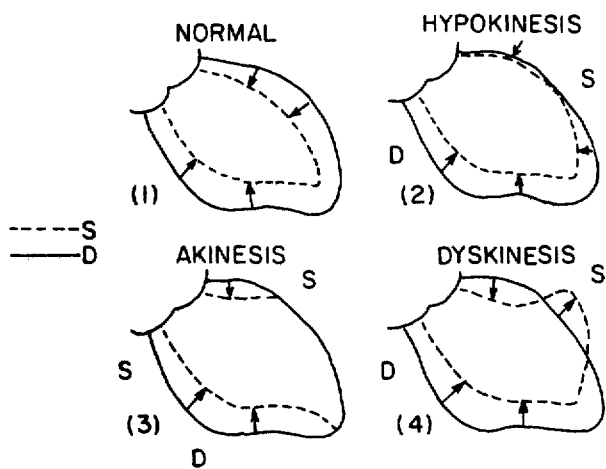
Figure 5B:
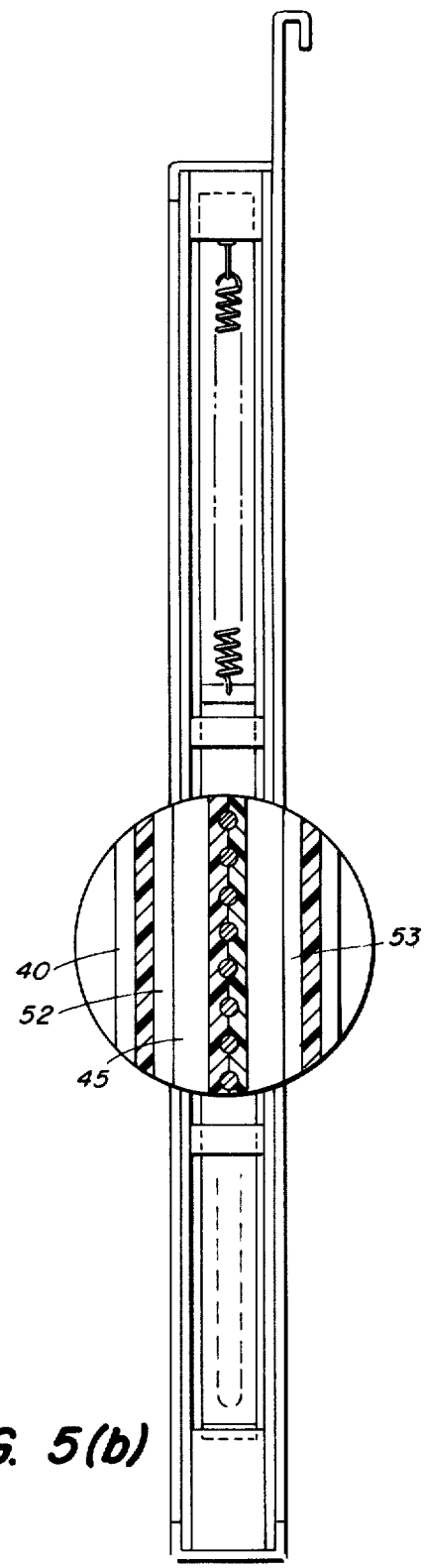
Figure 5A:
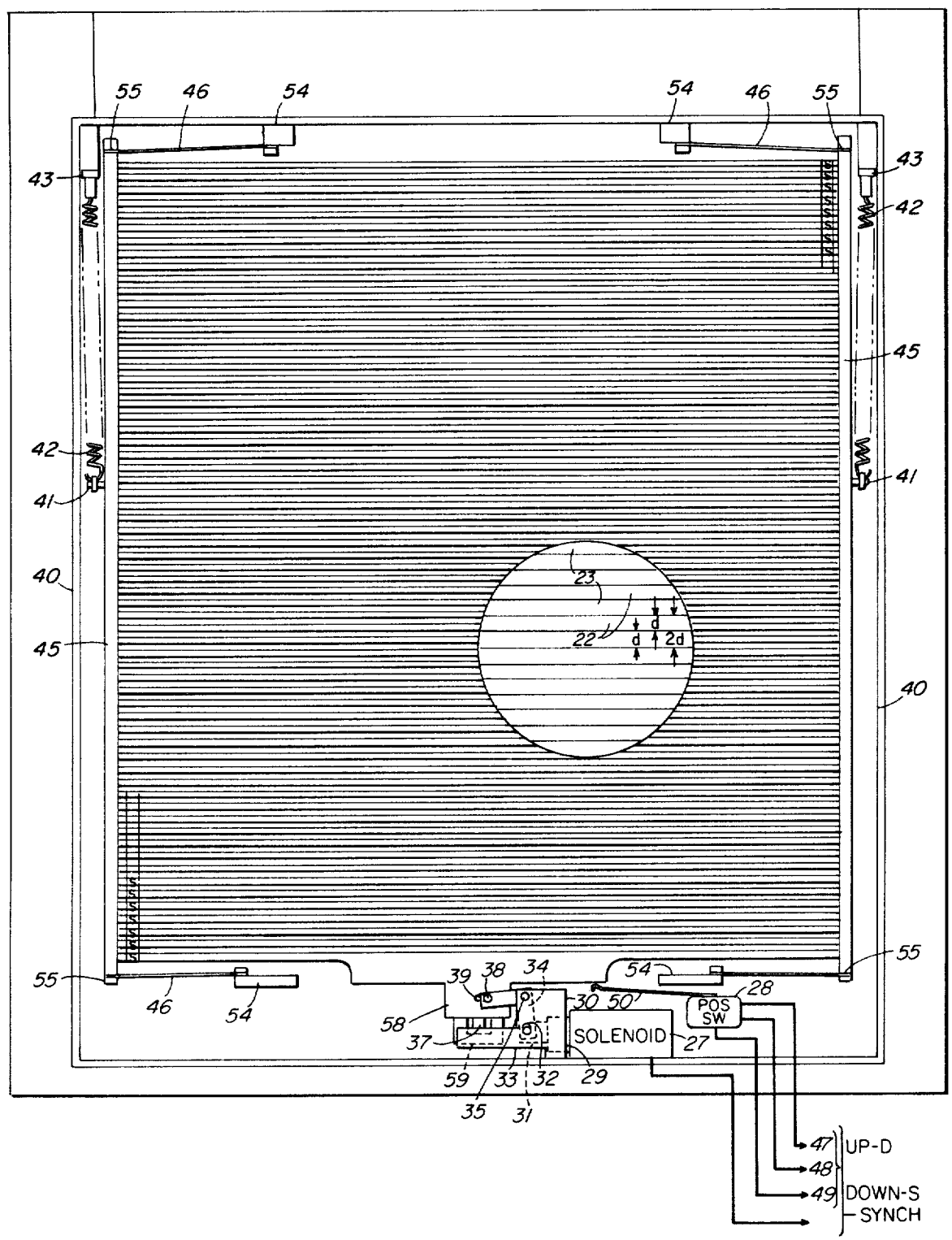
Figure 6A:
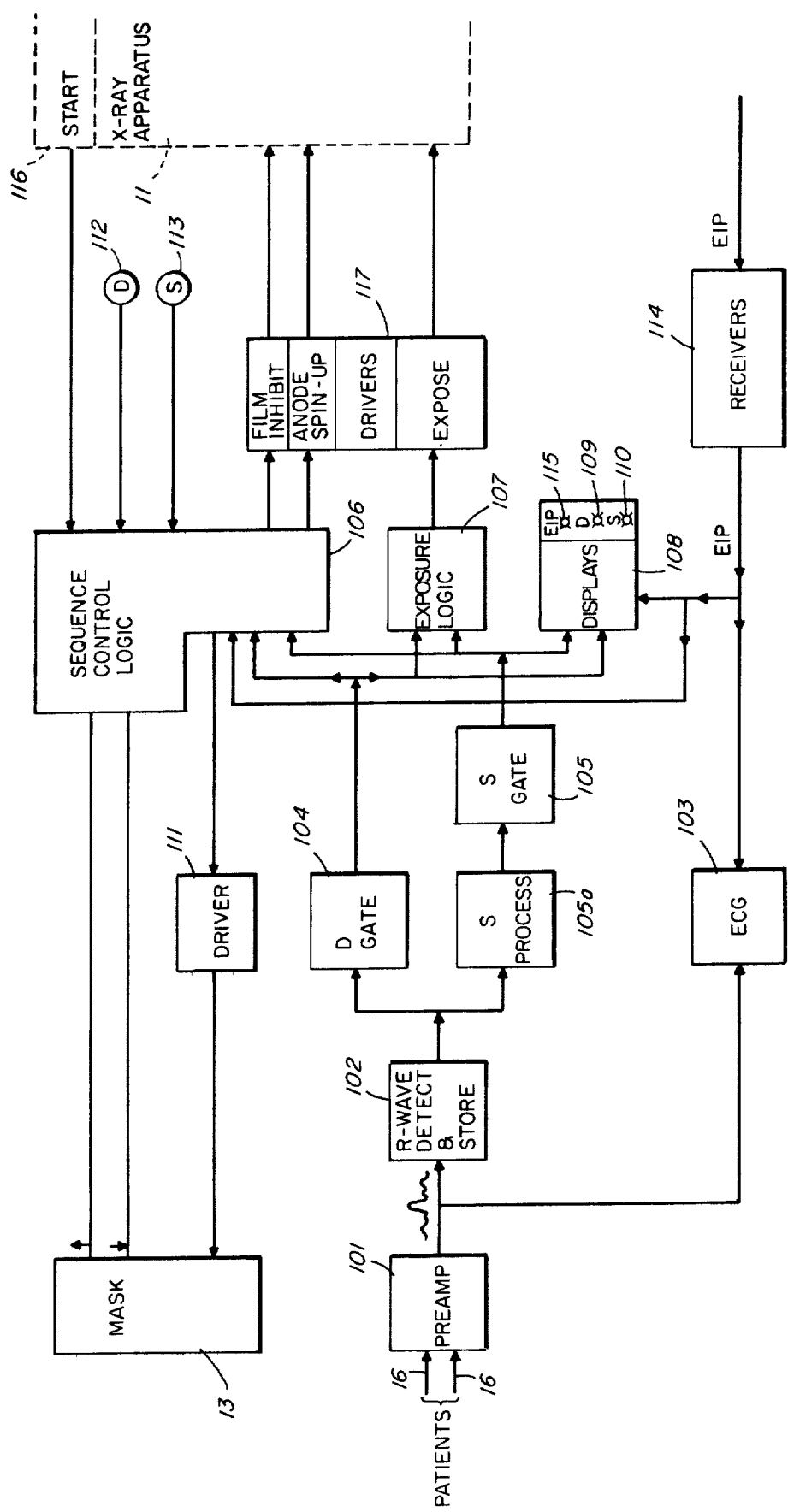
Figure 6B:
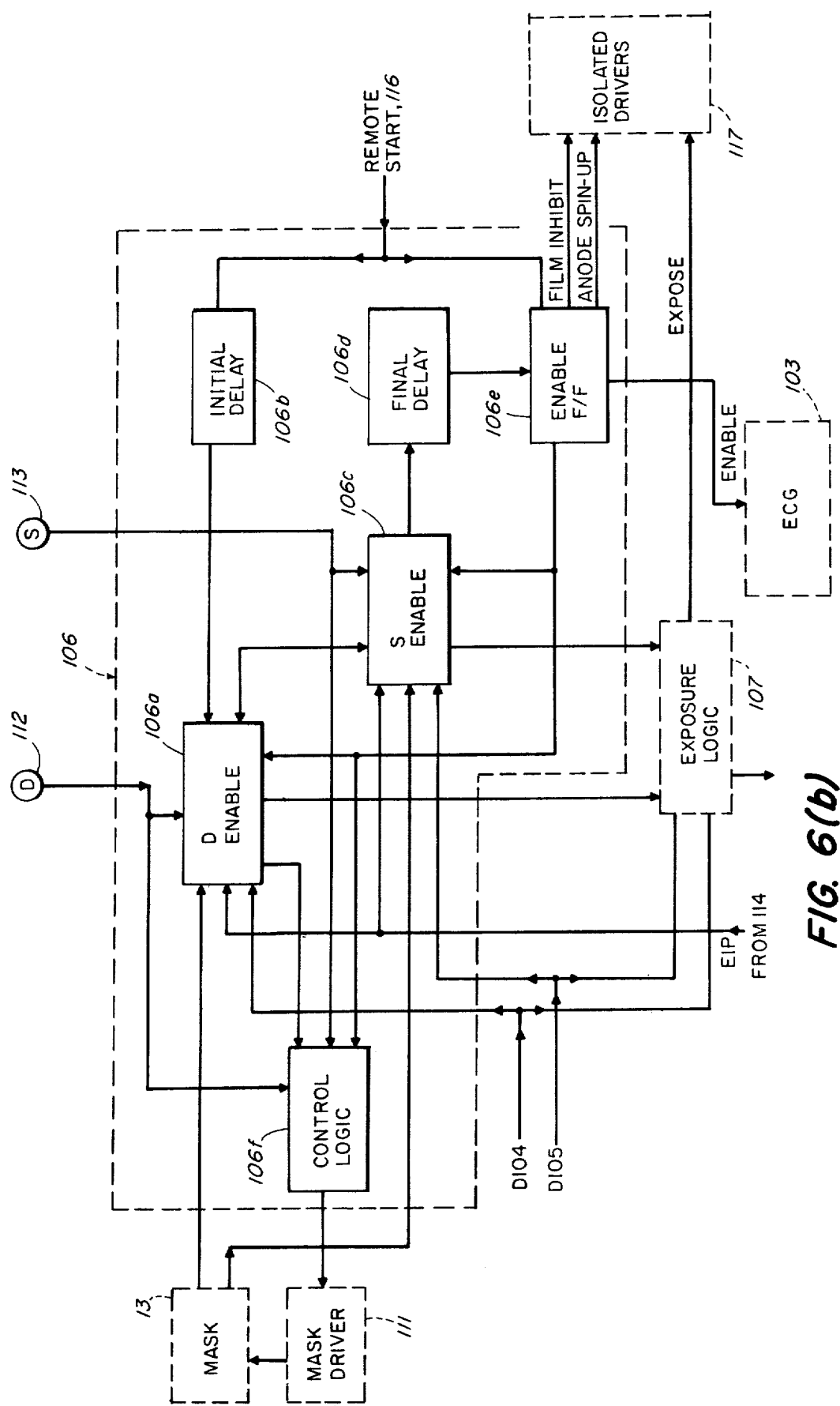

FIG. 4 is a group of schematic, outline drawings illustrating an X-radiograph, and its use, produced by the system of FIG. 1, FIG. 4(a) is a human heart at end diastole, FIG. 4(b) the heart is systole, FIG. 4(c) is the heart simultaneously at end systole and end diastole in accordance with the invention, and FIG. 4(d) shows systolic and diastolic outlines for (1) a normal heart, (2) hypokinesis, (3) akinesis and (4) dyskinesis;

FIG. f(a) is a front view, partially fragmentary, partly enlarged and schematic, of a masking frame useful in FIG. 1, FIG. 5(b) is an end view of the mask in FIG. 5(a), partially enlarged;

FIG. 6 is a schematic, block diagram illustration of preferred embodiments of the synchronizer in FIG. 1, FIG. 6(a) illustrates one mode of operation, FIG. 6(b) is a detailed block diagram of a logic circuit in FIG. 6(a), and FIGS. 6(c) and (d) are modifications of the synchronizer in FIGS. 6(a) and (b).

Figure 7A:
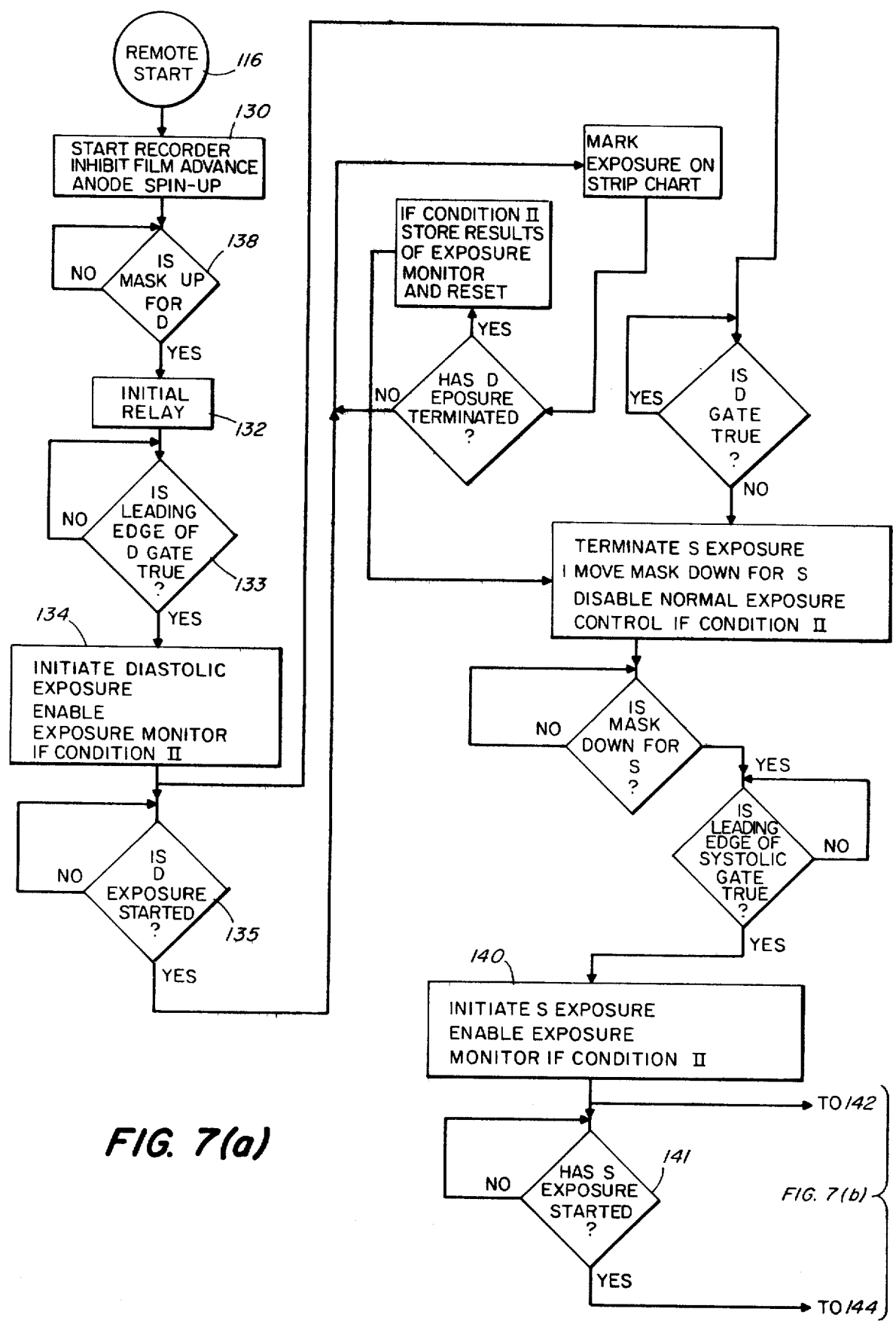
Figure 8:
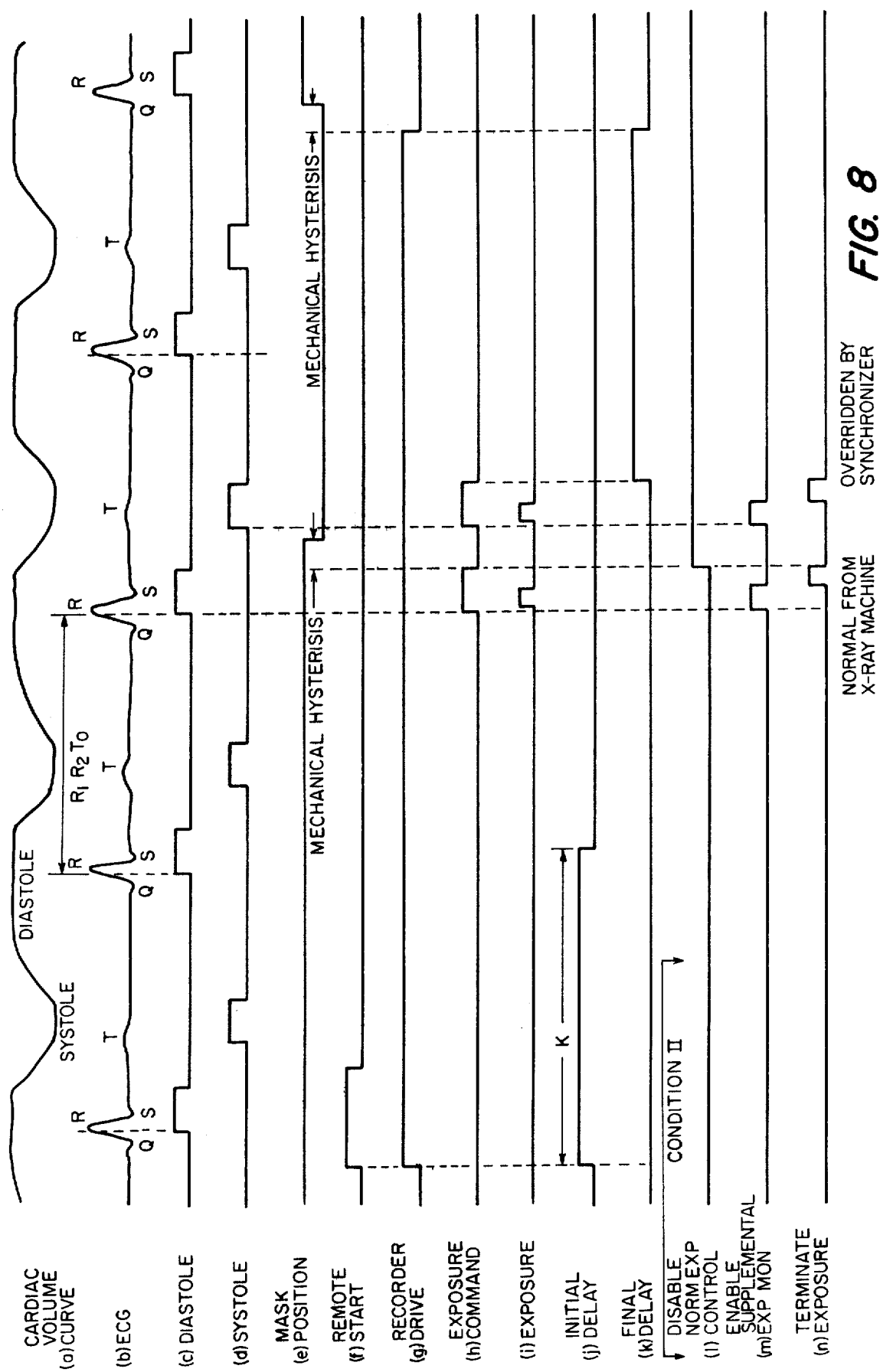
Figure 9:
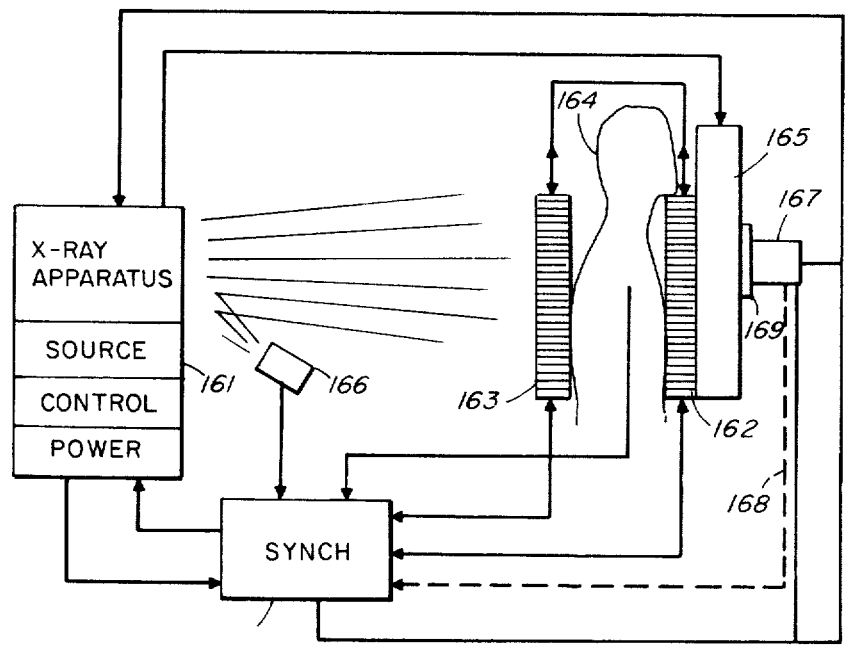
Figures 11, 12:
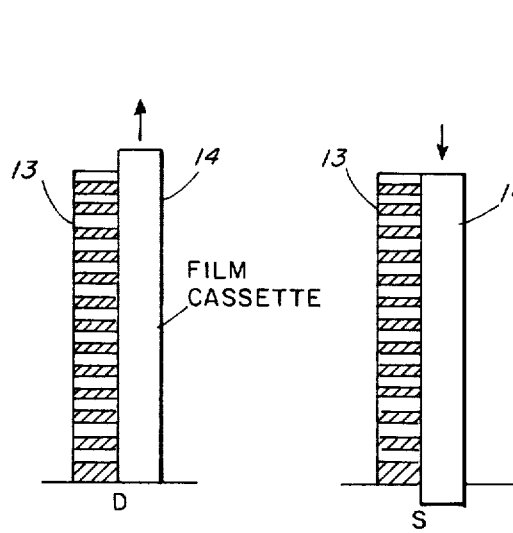
Figure 10:
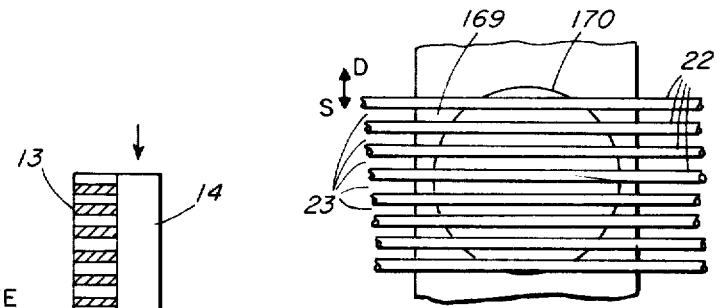
Figure 13:
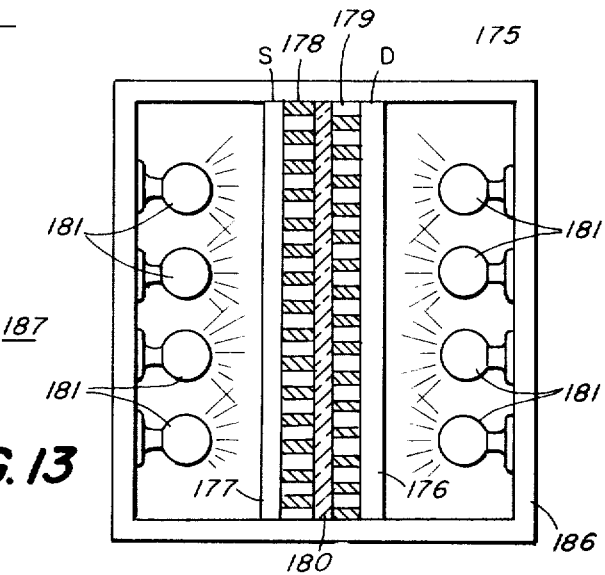
Figure 14:
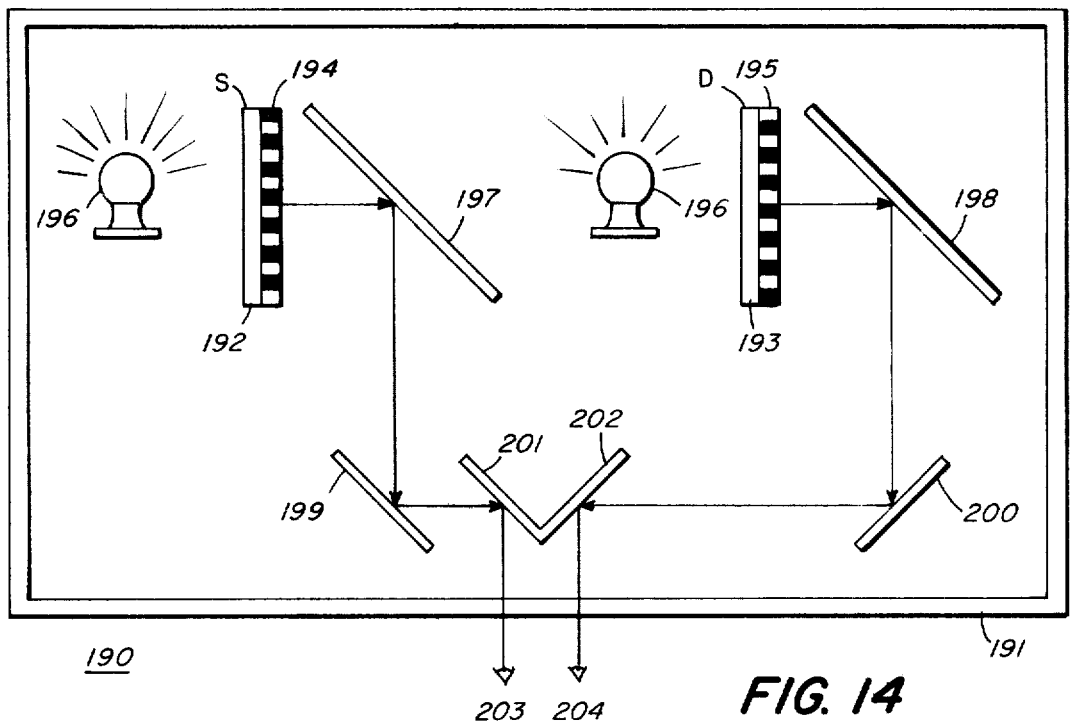
Figure 15:
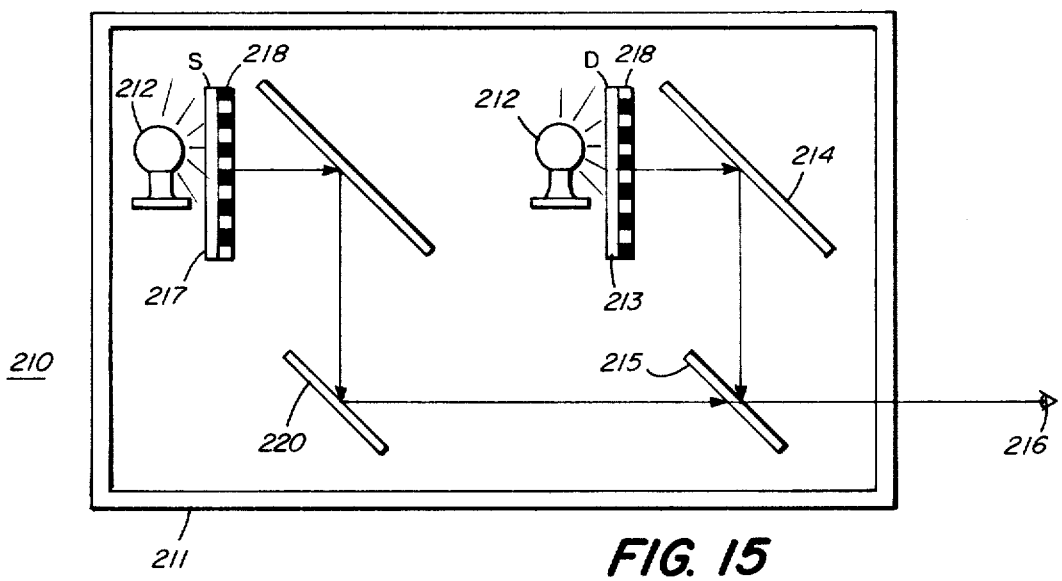

FIGS. 7(a) and (b) comprise a logic sequence flow chart of the synchronizer in FIG. 6;

FIG. 8 is a graph of timing signals associated with the synchronizer of FIG. 6;

FIG. 9 is a modification of the system in FIG. 1 illustrating alternate masking and photosensor positions;

FIG. 10 is a schematic view of a circular mask for a photosensor;

FIGS. 11 and 12 are end views illustrating relative mask versus film motion for use in the system of FIG. 1;

FIG. 13 is a plan view, shown schematic, of a contact printer light box for processing a composite photograph;

FIG. 14 is a plan view, shown schematic, of a light box for viewing a composite image of separate radiographs;

FIG. 15 is a plan view, shown schematic, of another light box for viewing a composite image of separate radiographs;

FIG. 16 is a schematic, block diagram illustrating an X-ray converter and display system;

FIG. 17(a) is an outline drawing of a heart left ventricle in end systole and end diastole;

FIG. 178b) is an enlarged portion of the radiograph in FIG. 17(a) illustrating discrete image elements;

FIG. 18 is a schematic block diagram illustrating a nuclear camera system for presenting three dimensional images;

FIG. 19 is an outline drawing in prespective illustrating a fluctuating object shown in three dimensions.

FIG. 20 is a sectional view of an object in FIG. 19;

FIG. 21(a) is a schematic illustration of a single slit mask operated by a stepping motor;

FIG. 21(b) is an end view in section of the mask in FIG. 21(a) taken along the line A—A'; FIG. 22(a) illustrates a modification of the mask and stepping motor in FIG. 21; and FIG. 22(b) is an end, sectional view of the mask in FIG. 22(a) taken along the line B—B'.

DESCRIPTION AND OPERATION OF THE SYSTEM IN FIGS. 1-4

Referring now to FIG. 1, there is here illustrated an X-radiation system for practicing the method of the invention. The system is generally indicated at 10. An X-ray apparatus 11 includes a source of X-radiation 61 directed to the chest of a patient 12. The apparatus 11 and patient 12 are radiation coupled through a masking frame 13 to radiographic film in a film cassette 14. A physiological synchronizer 15 incorporates an electrocardiograph which produces an electrocardiographic signal derived through electrodes 16 from the patient 12. the synchronizer produces an electrocardiogram 15A and is coupled to the apparatus 11 as shown. The synchronizer is also coupled to the masking frame 13 and the film cassette 14. The masking frame 13 and film cassette 14 are shown in perspective and in position for a diastolic exposure.

Figure 2:
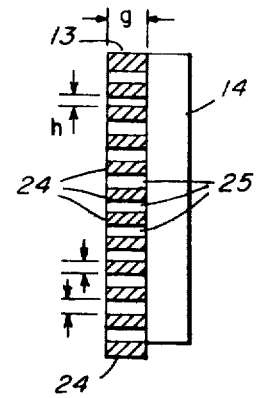
FIG. 2 shows the mask of the system in FIG. 1 in position for exposing a systolic image.
Figure 3:
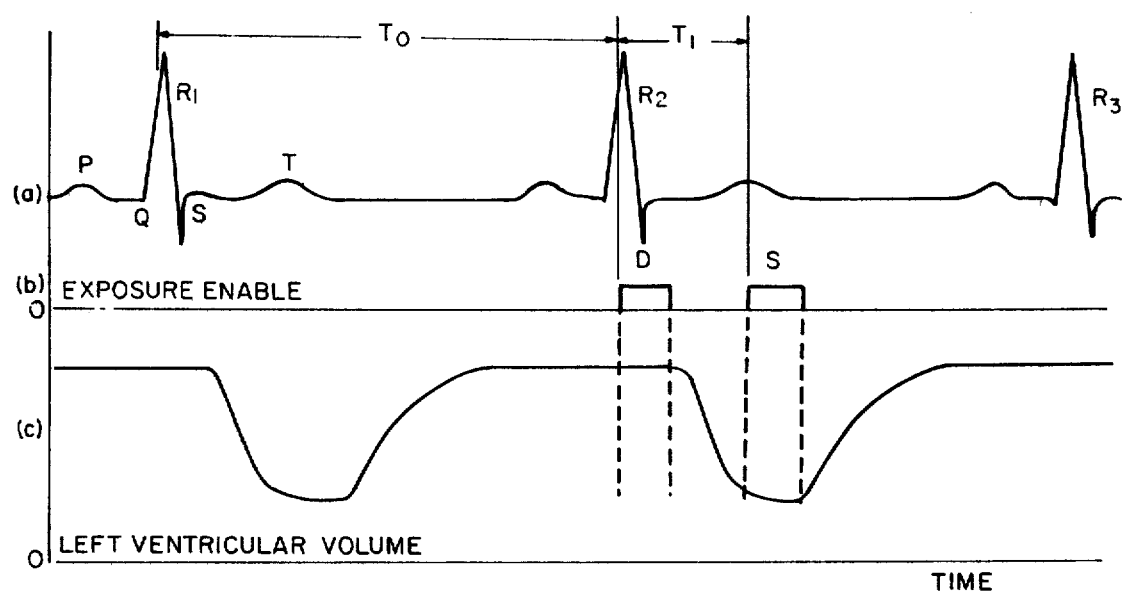
FIG. 3 is a group of graphs illustrating an electrocardiogram, relative to X-radiation exposure enable control and ventricular volume, in the operation of the system of FIG. 1.

The masking frame 13 in FIG. 2 is shown in position for systole relative to the film cassette 14. As shown in FIG. 3 the thickness g and slit width h may be proportionately varied to provide any degree of antiscattering, that is, collimating of the X-ray beam. Since the reduction of undesirable scattering radiation, that is, uncollimated radiation, serves to increase the contrast of the image in the radiograph, the exposure necessary for a good image tends to be reduced. Furthermore, by a suitable choice of the g:h ratio, any degree of antiscattering desired may be obtained. In the film cassette, as described in the above referenced Jaffee et al article, an antiscattering screen is required. Such a screen has a very substantial insertion loss, requiring an effective increase of patient irradiation of the order of 50%. By substituting a mask having suitable antiscattering properties the patient dosage may be considerably reduced. Thus using a single such mask, with two exposures, the total exposure is less than the expected sum of two noraml exposures.

The mask 13 has alternate parallel bars 24 and slits 25 of equal widths, as shown. That is to say the exposure area presented by the slit 25 is equal to the absorption area presented by the bar 24. The frame is movable vertically, as shown, to expose substantially half the area of presentation of the radiographic film 21 at end diastole, and the other half during end systole, after the mask is suitably repositioned a distance h. The slits of the mask 13 correspond with and define respective parallel area segments of the radiographic film.

In FIG. 3(a) an electrocardiogram is presented showing the elements of the QRS complex. In FIG. 3(b), the corresponding timing signals for controlling the occurrence of X-radiation are shown. In FIG. 3(c) a graph of ventricular expansion and contraction is shown correlated with FIGS. 3(a) and 3(b). The diastolic gate or timing signal is indicated D; the systolic S. The diastolic gate is initiated by the $R_2$ wave and the systolic gate is initiated proportional to $T_O$, the timing between the preceeding successive two R waves, $R_1$ and $R_2$.

In FIG. 4(a) a radiograph 18 is shown illustrating an organ 19 at the time of end diastole. In FIG. 4(b) the organ 19 is shown in a radiograph 20 at the time of end systole.

In a radiograph 21 of FIG. 4(c) the organ is presented, as shown, in both end diastole and end systole simultaneously, in accordance with the present invention. Here every other discrete area segment corresponds with a discrete image element; the diastolic elements 22 and the systolic elements 23 alternate, as shown, in parallel bands.

The resultant discrete diastolic and systolic images appear in juxtaposed image elements, interdigitally in bands, corresponding with the respective area segments. The diastolic and systolic images are thus presented in an interlaced pattern. The organ outlines are serrated, readily presenting the relative displacement between diastole and systole as shown at 26. The outline drawings of FIG. 4 are taken from actual angiographs depicting the left ventricle and aorta in end systole and end diastole.

The schematic presentations in FIG. 4(d) illustrate the relative wall outlines of the left ventricle in end systole and end diastole. The drawings cover (1) the normal heart displacement, (2) the heart in hypokinesis, less than normal motion, (3) the heart in akinesis, partially in no motion and (4) the heart in dyskinesis, motion contrary to normal where the left ventricle wall extends, in part, beyond the wall in diastole; the wall outlines actually cross over.

Operation

The operator interconnects the patient 12 with the electrodes 16 to the synchronizer 15. At that time the mask 13 is in the position shown in FIG. 1 for end diastole. The operator selects the exposure time and enables the synchronizer 15, which then assumes control of initiating the X-radiation. The strip chart recorder in the synchronizer 15 produces an electrocardiogram 15a. The synchronizer verifies the R wave and receives the QRS complex or ECG signal, shown in FIG. 3, curve (a), from the patient 12, stores the time between the R-waves of the previous cardiac cycle and then initiates the diastole timing gate D as shown in FIG. 4, curve (b). The gate D is wide enough to permit of an exposure sufficient to cover the useful range required, for example, 40–80 milliseconds. The exposure is chosen at the time of minimum cardiac motion during diastole and systole. Typically the timing gate for diastole is 100–130 milliseconds which, at the end of the timing signal D, irrespective of the selection chosen by the operator, the X-ray source 11 is disabled and the exposure is terminated.

As shown in curve (a), the interval $T_O$ from $R_1$ and $R_2$, the previous cardiac cycle, is stored. At the end of the interval coinciding with at least 80% of the rise time of the $R_2$ wave, the diastolic gate, as shown in curve (b), initiates the exposure. The X-radiation continues until terminated internally by the X-ray apparatus or the end of the gate D, whichever occurs first.

The systolic timing gate signal S, FIG. 4, curve (b), in internally generated by the synchronizer 15. The center of the gate S is chosen substantially to coincide with end systole which typically occurs approximately at the time of the T wave in the QRS complex, as shown in the curve (c) of FIG. 3.

Here the synchronizer generates the systolic gate at a time t preferably chosen in accordance with:

$$t = a + bT_O \qquad \text{Equation 1}$$

where $a=140$, $b=2$, $T_O$ is the period of the previous cycle an all values are in milliseconds.

For an average heart pulsation rate of 60 beats per minute, the period $T_O$ is one second, diastole may be 600–800 milliseconds and systole 200–400 milliseconds.

The S gate is the same pulse width as the D gate. As with the diastolic gate D, the gate S initiates the systolic exposure; the exposure again is terminated internally by the X-ray apparatus or the end of gate S, whichever occurs first.

The patient then is X-irradiated during the peirod of the diastolic gate D, as in FIG. 4, curve (b), and then again during the period of the systolic gate S in curve (b). The X-radiation from the patient passes through the masking frame 13 to expose one-half the area of presentation of the film in alternate bands to produce a diastolic image. During systole the masking frame is repositioned in such a manner as to mask the previously exposed areas of the film, the remaining half being exposed in alternate bands corresponding with the systolic image.

The film is then developed to provide the diastolic and systolic images in the interlaced pattern of juxtaposed, interdigital diastolic and systolic image elements. Each systolic band or area segment is preferably indexed, as shown, to discriminate the diastolic image elements from the systolic.

As shown in FIG. 1, the synchronizer is coupled to the film cassette. In the typical modern installation the film cassette automatically changes film at the end of each exposure. The synchronizer inhibits the film chaange to allow for a second exposure on the same film. At the end of the second exposure, the automatic film change is allowed to operate.

The organ shown in the radiographs of FIG. 4(c) may, for example, be the heart outline, in particular, the wall of the left ventricle. Since, as noted above, the image outlines appear serrated, the radiologist can readily derive a measure of the wall displacement at a glance.

With an 11×17 radiograph prepared in accordance with the invention where the left ventricle outline displacements were of the order of 3-5 millimeters, the serrations were clearly apparent from a distance of 30 feet. The typical bands as used in the preferred embodiment are 3 millimeters wide, and indicia at the ends of the bands identifying systole as S, enable the radiologist readily to distinguish the diastolic image elements and outlines from the systolic.

DESCRIPTION OF THE MASK IN FIG. 5

Referring now to FIGS. 5(a) and 5(b) there is here illustrated a masking frame and housing assembly. The mask has a plurality of cylindrical rods embedded in spaced, parallel relation in a rigid plastic slate. An end view is shown in FIG. 5(b) of the mask.

The diameter of each rod is equal to each slit formed by the space between each pair of rods. The mask is affixed to a pair of end support members in frictionless, flexing attachment to the housing to maintain the mask suspended with motion restricted to the vertical axis. A pair of springs connected between the housing and end support members hold the mask normally in an extreme upward position for the diastolic exposure.

A solenoid mounted to the housing is electrically coupled to the synchronizer and mechanically coupled to the mask to move the mask vertically downward against the restraining force of the springs for the systolic position. A mask position switch, coupled to the synchronizer, senses the vertical position of the mask. A pair of identification masks are mounted in the housing in fixed position adjacent the mask to expose indicia correlated with systolic exposure.

Thus the rods 22 are rigidly embedded in spaced relation in the plastic plate 51. The plate is inserted into channels formed in the end members 45 and rigidly adhered thereto. Each rod 22 has the same diameter d as the width of each slit 23. The total period from the edge of one rod to the edge of the next is then 2d, as shown. The rods are chosen to be cylindrical to minimize edge effects between image elements.

The mask is flexibly secured to the housing 40 by four resilient suspension elements 46. Each element 46 is firmly attached at one end to fastener 54 secured to the housing. The other end of each element 46 is attached to the end member 45 by a clamp 55.

Each of a pair of restraining springs 42 is fastened at one end to a fastener post 43 fixed to the housing 40 at the upper corners, as shown. The other end of each spring 42 is attached to a fastener post 41 affixed to each member 45.

A solenoid 27 has a threaded shaft 29 affixed in threaded engagement to a bracket 30 mounted on the housing 40 below the mask, as shown. An armature 31 of the solenoid is coupled through an L-shaped rocker lever 34 to a central extension piece 58 affixed to the mask. Actuator pin 33 extends from the lever 34 into a slot 32 in the armature 31. The corner of the lever 34 has a bearing point about a pivot pin 35 extending from the bracket 30. Affixed to the upper left arm, as shown, of the lever 34 is an actuating pin 38 which travels in a slot 39 formed in the lower piece 58 of the mask. A U-shaped bracket 59 is attached to and extends below the piece 58. A stop bar 37 affixed transversely to the bracket 30 limits the vertical motion of the mask.

The mask is normally in position for diastole. Here the mask is shown in position for systole and the solenoid 27 actuated with the armature 31 withdrawn into the solenoid.

The solenoid is actuated in response to a signal from the synchronizer after the diastolic exposure has been complete to pull the frame down in position against the restoring force, through the rocker lever 31 linkage, of the springs 42 to meet the bar 37, as shown. When the solenoid 27 is deenergized after the systolic exposure has been taken, the armature is restored to the right, as shown, allowing the springs 42 to move the mask upwardly, limited by the stop bar 37 and bracket 59. A single pole, double throw mask position switch 28, mounted between the cover plates 52 and 53, has a lever arm 50 which contacts the mask. The switch 28 responds to provide a signal at its output terminals 47 and 48 indicating the mask to be in the upward or diastolic position. Conversely when the mask is down, as shown, a signal from the terminals 48 and 49 indicates that it is in the position for systole. The signal from the position switch 28 is coupled to the synchronizer, as will be described further below.

Figure 7B:
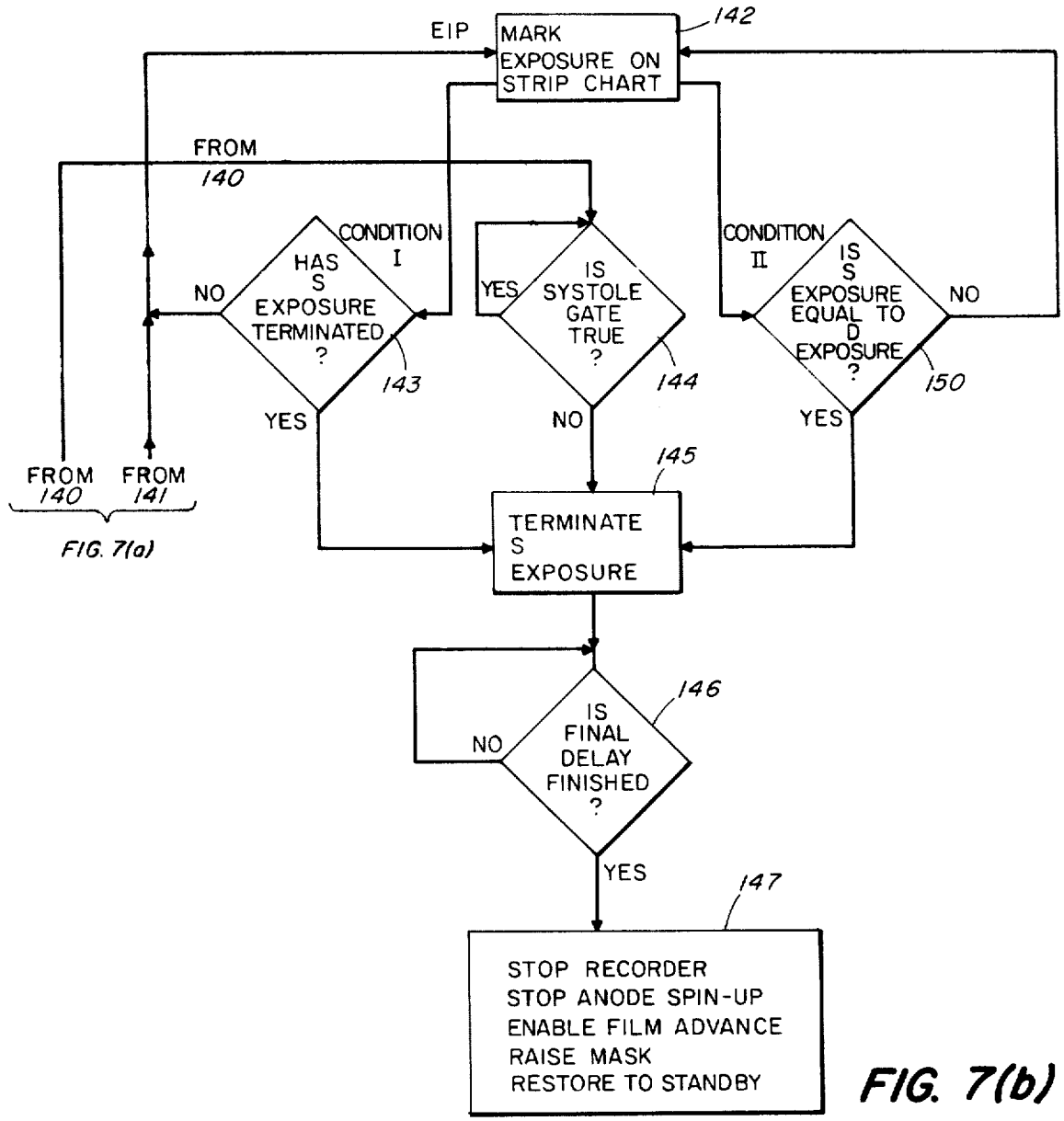

Description and Operation of the Synchronizer in FIGS. 6–8

Referring now to FIG. 6(a), there is here illustrated a schematic, block diagram of the physiological synchronizer as used in the present invention. The basic synchronizer used in the preferred embodiment is a modification of the synchronizer described and illustrated in the above referenced U.S. Pat. No. '360, incorporated herein.

The modified synchronizer has two principal modes of operation. In both modes, the command to initiate the radiation exposure is taken away from the X-ray apparatus and assumed by the synchronizer. In one mode of operation, the primary control of exposure termination is contained within the X-ray apparatus. The synchronizer initiates the exposure which takes place for a selected period determined by the operator. In the event that the exposure is within the enabling time as provided by the synchronizer timing gates, the termination of the exposure takes place on command from the X-ray apparatus. If the exposure tends to exceed the enabling time, then the termination is affected by the synchronizer.

In the other mode of operation the synchronizer, in combination with a sensing device, either part of the X-ray apparatus or provided separately, determines the photon count for the first or diastolic exposure and stores that count. The systolic exposure is controlled substantially to equal the diastolic photon count during the second exposure; when the second exposure photon count is equal to the first one, the exposure is terminated. In another variation of the mode of operation, the elapsed time for the initial photon count is stored. The actual length of systolic exposure time is then controlled to equal the elapsed time of the first exposure. In a variation of this mode, the synchronizer counts and stores the actual length of the first or diastolic exposure time. The actual length of systolic exposure time is controlled to equal the diastolic exposure time.

The QRS complex is received by the synchronizer and coupled to an isolated preamplifier. The output of the amplifier is coupled to an R-wave detector and verifier circuit and to a strip-chart recorder of an electrocardiograph. The R-wave detector, given the presence of an R-wave, is then coupled to a diastolic or D gate generator and a systolic or S gate generator. The diastolic and systolic gate generators are coupled to a sequence control logic circuit, an exposure logic circuit and thence to a display circuit. An input to the sequence control logic circuit is derived from a remote start switch in the X-ray apparatus, upon actuation by the operator. A further input to the sequence control logic is from diastole only command and/or systole only command switches located at the synchronizer. An output of the sequence logic circuit is coupled to a mask driver circuit which is coupled to the mask. An output of the mask circuit is coupled back to the sequence control logic circuit. Another output of the sequence control logic circuit is coupled to isolated drivers which couple film advance inhibit, anode spinup, and exposure command signals to the X-ray apparatus. An output of the exposure logic circuit is coupled to the isolation driver circuit. The exposure in progress or EIP signal is derived from the X-ray apparatus and coupled through an isolated receiver to the strip chart recorder. The EIP signal is also coupled from the receiver to the display circuit which indicates EIP. The display circuit has indicators for the diastolic and systolic gates.

In the case where the synchronizer counts the elapsed time of the exposure and stores that count, an exposure duration counter circuit is included coupled to an isolation transmitter-receiver circuit. Both of those circuits receive input signals from the sequence control logic circuit. The EIP signal from the receiver is coupled directly to the exposure duration counter. The exposure duration counter is also coupled to the exposure logic circuit. The isolation transmitter-receiver is coupled in both directions to an exposure command monitor in the X-ray apparatus.

In the case where we wish to normalize the exposures in terms of integrated X-ray flux, the X-photons for the first exposure are converted into electrical signals and coupled by a photon transducer through a preamplifier to an integrator to produce a signal indicative of the count. An input to the intergrator is derived from an optically isolated transmitter-receiver which is coupled in both directions to the exposure command/monitor in the X-ray apparatus. The output of the integrator is coupled to a peak detector circuit which derives an input from the sequence control logic circuit. The outputs of the peak detector and integrator are applied to a comparator which is coupled to the sequence control logic circuit to produce a signal coupled to the exposure logic circuit. Another output of the comparator is coupled to the isolation transmitter-receiver circuit, which receives a further input from the sequence control logic circuit.

Condition I—Exposure Termination Control in X-Ray Apparatus

Referring now to FIG. 6(a) there is here generally illustrated the modified synchronizer, as indicated at 100, for use in the preferred mode of the invention.

A pair of electrodes 16 are shown coupled from the patient to a preamplifier 101. One output of the amplifier is coupled to an R-wave detector circuit 102 and the other output to a strip-chart recorder in an electrocardiograph 103. The detector 102 is coupled to a diastolic gate generator 104 and, through a systolic interval process circuit 105(a), systolic gate generator 105. The D gate is coupled to a D exposure enable circuit 106(a) in a sequence control logic circuit 106, an exposure logic circuit 107, and a display circuit 108 with a diastole indicator light 109.

The sequence control logic circuit 106 is shown in detail in FIG. 6(b). It includes a diastolic exposure enable circuit 106(a), an initial delay circuit 106(b), a systolic exposure enable circuit 106(c), a final delay circuit 106(d), an enable flip-flop circuit 106(e), and a mask control logic circuit 106(f).

The logic circuits 106(a)-106(f) within the sequence control logic circuit 106, as shown in FIG. 6(b), are coupled together as follows:

The delay circuit 106(b) has an output coupled to the enable circuit 106(a). The enable circuit 106(a) is bidirectionally coupled to the systolic enable circuit 106(c). An output of the diastolic circuit 106(a) is coupled to the input of the mask control logic circuit 106(f). The systolic or S exposure enable circuit 106(c), the diastolic circuit 106(a) and the mask control logic circuit 106(f) are each coupled to the output of the enable flip-flop circuit 106(e). The delay circuit 106(d) is coupled to the input of the flip-flop circuit 106(e) and derives an input from the systolic exposure enable circuit 106(c).

The S gate is coupled to the S exposure enable circuit 106(c), the exposure logic circuit 107, and the display circuit 108 to a systole indicator light 110. An output of the mask control logic circuit 106(f) is coupled to a mask driver circuit 111 to energize the solenoid 27 in the mask assembly of FIG. 5(a) to position the mask 13. Outputs from the mask position switch 28, shown in FIG. 5, are coupled to the D exposure enable circuit 106(a) and S enable 106(c), as shown, indicating mask position.

A manual diastole only command switch 112 on the front panel of the synchronizer is coupled to the D enable 106(a) and mask logic 106(f). A manual systole command switch 113 is coupled to the enable 106(c) and mask logic 106(f). An exposure in progress, EIP, signal is derived from the X-ray apparatus and coupled to an isolation receiver circuit 114 which in turn is coupled to the strip-chart recorder 103 to provide exposure event marks correlated with the electro-cardiogram. The EIP signal from the receiver 114 is also coupled to the display circuit 108 to the EIP light 115.

A remote start switch 116 located in the X-ray apparatus is coupled to the delay 106(b) and enable 106(e). The logic circuits 106(e) and 107 are coupled to the drivers 117. The driver circuit 117 produces the film advance inhibit, the anode spinup and the exposure command signals for coupling to the X-ray apparatus 11.

Condition II—Synchronizer Terminates Systolic Exposure

Referring to FIG. 6(c) for the case where the synchronizer determines the exposure time of the first exposure and then controls the exposure time of the second exposure in accordance with that stored count, an exposure duration counter circuit 120 is coupled to a transmitter-receiver circuit 121. The circuit 121 is coupled to the exposure in progress and control circuits in the X-ray apparatus. The circuit 12 derives an input from the S exposure enable circuit 106(c) and the counter 120. The counter 120 receives an input from the exposure logic circuit 107 and from the isolation receiver 121.

In FIG. 6(d), an actual count of the X-photons for the first exposure is compared with the X-photon count for the second exposure until they are equal and the synchronizer totally controls the second exposure. For this case, an X-ray transducer 122 is coupled to a preamplifier 123 and integrator 124. The integrator has an output coupled to a peak detector 125 and a comparator 126. The detector 125 and comparator 126 each derive an input from the exposure logic circuit 107. An output of the comparator 127 is coupled to the exposure logic circuit 107. A transmitter-receiver circuit 127 derives an input from the sequence control logic circuit 106. A bidirectional signal is coupled from the circuit 127 to the X-ray apparatus exposure in progress and control circuit. An output of the circuit 127 is coupled to the integrator 124.

Referring now to FIG. 6(e), there is here illustrated an exposure in process, EIP, signal circuit for internally developing an EIP signal. When no such signal is available in the X-ray apparatus, this circuit is added as a modification to the synchronizers.

Thus an X-ray transducer 152, such as a photomultiplier tube, is coupled to a preamplifier 153 and threshold comparator 154. The output EIP signal can then be used in place of the output of the receivers 114 in FIG. 6(a) or the receiver 127 in FIG. 6(d).

Operation—Condition I

The power is turned on and the system in FIG. 1, including the mask of FIG. 5 and synchronizer of FIG. 6(a) and (b) is in a standby condition. The operator couples the electrodes 16 to the patient. An ECG signal is at that time coupled to the preamplifier 101 and R-wave detector 102. If there is in fact a QRS complex wave at the input of the detector 102, the R-wave exceeds a preselected threshold level. The detected value of the first R-wave increases the threshold to approximately 80% of the amplitude of the first R-wave. The threshold tends to decay since it represents, for example, the voltage from an RC network. The next R-wave to come along must exceed the new threshold level to enable the diastolic and systolic gate generators 104 and 105. Thus once the electrodes are coupled to the patient, the QRS signal is presented to the electrocardiograph 103 and the R-wave detector circuit 102. This has the effect of continuously producing D and S timing signals from the generators 104 and 105 and QRS signals to the ECG 103. However, nothing else happens at that point until the remote start switch 116 is pressed by the operator. In particular the mask is in the up position, ready for a diastolic exposure, the electrocardiograph 130 strip chart recorder is disabled, the film inhibit, anode spinup and exposure commands disabled.

After the operator presses the remote start switch 116, the sequence as shown in FIGS. 7(a) and (b) is initiated for Condition I. The enable flip flop 106(e) and initial delay circuit 106(b) then change logic state. The enable circuit 106(e) signals a change in state to the driver circuit 117 to produce the film advance inhibit and anode spinup signal directed to the X-ray apparatus. At the same time the output of the enable circuit 106(e) activates the strip-chart recorder in the ECG 103. At this point the exposure sequence is inhibited by an output from delay circuit 106(b) inhibits D enable 106(a) thereby inhibiting S enable 106(c).

Pending the end of the initial delay signal, curve (j) in FIG. 8, the enable flip-flop 106(e) sets the D exposure enable 106(a), S exposure enable 106(c) and the mask control logic 106(f). When the delay 106(b) signal terminates, the inhibit of the D exposure enable 106(a) is removed, returning control of S enable 106(c) to D enable 106(b). If the D switch 112 is selected and the mask is up, the next diastolic signal that comes along, the leading edge of the next D gate, curve (c) of FIG. 8, allows the exposure logic 107 to pass a D expose signal to the drivers 117 and enable the X-ray machine to initiate the D exposure. The enable 106(a) allows the systolic exposure enable 106(c) to accept a systolic S gate, curve (d) FIG. 8. When the diastolic exposure terminates, curve (i) FIG. 8, the EIP signal is removed and the D circuit 106(a) produces a signal to mask control logic 106(f) to activate the mask driver 111 and energize the solenoid 27, in FIG. 5(a), to position the mask down for an S exposure. A down signal from the mask position switch 28, in FIG. 5(b), allows the S enable 106(a) to respond to the next S gate, if the S switch 113 has been selected by the operator. The leading edge of the next S gate removes the inhibit condition from the S enable. This enables exposure logic 107 to pass a S exposure gate, curve (h) FIG. 8, to the drivers 117 and exposure command to the X-ray machine. When the S exposure is terminated, the EIP signal is removed, disabling D enable 106(b) and enable 106(c). The final delay 106(d) signal is initiated to remove the film advance inhibit and anode spin-up command signals to return the control of film advance to the X-ray apparatus and stop anode spin. The termination of the final delay signal, curve (k) FIG. 8, returns the D and S enable circuits 106(b) and 106(c) to standby and deenergizes the solenoid 27 to allow the mask to return to its normal up position for a D exposure.

Operation—Condition II

In Condition II the S exposure termination control in the X-ray apparatus is removed, curve (e) FIG. 8. The synchronizer exercises control over S exposure termination in accordance with the D exposure.

In the modification of FIG. 6(c), the counter 120 receives an EIP signal from the receiver 12 and, in response to a signal from exposure logic 107, curve (m) FIG. 8, monitors the period of the D exposure. Where D exposure is terminated by a signal from the X-ray apparatus, curve (n) FIG. 8, to logic circuit 107 disables the exposure termination control in the X-ray apparatus. The counter stores the elapsed time of the D exposure, and in response to EIP from the receiver 114, signals the exposure logic 107 to terminate the S exposure at such time as the S exposure equals the D exposure.

In FIG. 6(d) the modification shown operates to monitor and store the photon count during the D exposure and terminate the S exposure when the D and S counts are equal. The transducer 122, preamplifier 123 and integrator 124 monitor and sum the D photon count, which is stored in the peak detector 125. During the S exposure, the S photon count signal is coupled from the integrator 124, in response to the EIP signal from the X-ray apparatus, to the comparator 124. A signal from the exposure logic 107 enables the detector 125, and comparator 126, to couple a signal representative of the D exposure to the comparator 126. An output from comparator 126 to the transmitter 127 and the X-ray apparatus terminates the S exposure. The S enable 106(c), in response to termination of the D exposure gate, couples a signal to the transmitter 127 to disable the X-ray apparatus exposure termination control during systole.

Description and Operation of the System In FIGS. 9 and 10

Referring to FIG. 9 a modification of the system in FIG. 1 is illustrated. Here a synchronizer 160 is coupled to an X-ray apparatus 161 and a pair of masking frames 162 and 163. As shown in FIG. 9, masks 162 and 163 are controlled by the synchronizer 160. A patient 164 is positioned between the masking frames and a film cassette 165 adjacent, as shown, to the mask 162. A photon sensor 166 is coupled to the synchronizer 160. The photon sensor 166 senses X-rays directly from the source 161. Another photon sensor 167 is positioned behind the film cassette 165, as shown, and is coupled to the apparatus 161. In one mode of operation the sensor 167 is coupled, as shown by the dashed line 168, to the synchronizer 160.

The photon sensor face is covered by a mask 169 with a circular opening 170 behind the mask bars 22 as shown in FIG. 10. Because of the circular opening of the mask 169, the motion of the masking bars from diastole to systole takes place substantially without changing the field of view of the photon sensor 167.

As described above the synchronizer controls the position of the mask 162 to synchronize with diastolic and systolic exposures, respectively. The effect of positioning a mask between the source of X-radiation and the patient is to limit radiation of the patient to those regions corresponding with the diastolic and systolic images, respectively.

The photon sensor 166 is positioned to receive radiation directly from the apparatus 161. In one mode of operation the output of the photon sensor 167 is coupled to the X-ray apparatus 161 and integrated to provide a photon count during a first, for example diastolic, exposure. The apparatus 161 is coupled to the synchronizer which stores the count. As described above, the synchronizer normally controls the initiation of the exposures, and the X-ray apparatus controls the termination of the exposures; provided, of course, that it does not exceed the enabling time controlled by the synchronizer diastolic and systolic gates, respectively.

Where, however, there is no provision in the apparatus for coupling to the photon sensor 167, the sensor 167 is coupled by the dashed line to the synchronizer 160 where the photon count for the first exposure is derived to terminate the first exposure in accordance with the operator's selection.

The photon sensor 166 is coupled to the synchronizer to provide a photon count for the first interval. The output of the photon sensor 167 as coupled to the apparatus 161 controls the termination of the first exposure. The synchronizer stores the photon count derived directly from the X-ray source 161 for the first exposure and then controls the second exposure to be substantially equal to the stored photon count derived from the sensor 166 for the first exposure.

In another mode of operation, a timing mechanism in the apparatus 161 controls the first exposure to terminate within the time allowed by the enabling gate from the synchronizer. During that time the synchronizer, through the sensor 166 and counting circuit in the synchronizer, monitors the radiation directly from the apparatus and stores a photon count signal for the first exposure. When the second exposure takes place, the synchronizer continues to monitor the photon count with the sensor 166 and a counting circuit in the synchronizer. When the second photon count substantially equals the first photon count, the second exposure is terminated by the synchronizer.

Relative Mask Motion—FIGS. 11 and 12

Referring now to the mask 13 and film cassette 14 as shown in FIGS. 11 and 12, another mode of operation of the system in FIG. 1 is illustrated. Here the mask 13 is fixed in position and the film cassette moves. This has the effect of exposing the same regions of the patient to the film at different times. This is to be contrasted with the system in FIG. 1 where the mask moves. exposing neighboring regions of the patient. In the system as shown in FIG. 1 the diastolic image is different from the systolic image in that juxtaposed image elements are, in fact, images of different, neighboring regions of the patient, taken at different times.

Here, the same region is taken twice, but at different times. Effectively, half the total image taken conventionally is eliminated in favor of comparing identical regions at different times.

Separate Radiographs—FIGS. 13–15

Referring now to FIG. 13 there is here schematically illustrated a contact printer light box generally indicated at 187. FIG. 13 is a plan view of the light box, with the cover not shown, the photosensitive film, two masks and two radiographs shown partly in section and oriented in planes normal to the plane of the drawing. One radiograph has a systolic image of an organ; the other has the diastolic image, as indicated.

Thus, the box 175 has a housing 186 in which are positioned a plurality of light sources 181. The systolic image is projected through the radiograph 176 and systolic mask 178 to the left side, as shown, of an exposed photo-sensitive transparency film 180. The diastolic image is projected through the radiograph 177 and mask 178 to the right side, as shown, of the film 180.

A plurality of light sources 181 are positioned as shown on both sides of the contact printer or light box.

The unsensitized photo film is shown in cross-section to distinguish it from the masks and the radiographic images on the systolic radiograph 166 and diastolic radiograph 167. Note that each of the masks 178 and 179 have fixed parallel bars 182 and slits 183 of equal widths. The bars 182 and slits 183 of the mask 178 are precisely out of phase with the bars 184 and slits 185 of the mask 179. When the exposure is made half of the sensitized film 180 receives a systolic image and the other half receives a diastolic image, with the image elements interdigitally juxtaposed to provide, after the film is developed, the systolic and diastolic images in an interlaced pattern as taught by this invention.

Referring to FIG. 14, there is here schematically illustrated a light box for viewing two separate radiographs, one taken during systole and the other taken during diastole in such a manner to provide the systolic and diastolic images in an interlaced pattern to an observer in the manner of the present invention.

The box is generally indicated at 190. A housing 191 has a systolic image radiograph 192 and a diastolic image radiograph 193 intimately in contact with a systolic mask 194 and diastolic mask 195, respectively as shown. A pair of light sources 196 illuminate the images through the radiographs and masks to a pair of 45 degree mirrors 197 and 198. The mirrors 197 and 198 couple the systolic and diastolic images to another pair of 45 degree mirrors 199 and 200, respectively. The images are coupled from the mirrors 199 and 200 to a pair of 45 degree coupling mirrors 201 and 202 for viewing by an observer as shown by the eyes 203 and 204.

With the lights on, the systolic image is transmitted through the mask 194 to the mirror 197, to the mirror 199, to the mirror 201 to the left eye 203, as shown, of an observer. The diastolic image is produced by light through the radiograph 193, the mirror 200 and a mirror 202 to the right eye 204, as shown, of the observer. The observer sees the images displaced in space and merges them with the image elements interdigitally juxtaposed to produce the systolic and diastolic images in an interlaced pattern in accordance with the instant invention.

Referring now to FIG. 15 there is here illustrated a light viewing box generally indicated at 210. A housing 211 carries a pair of light sources 212 for transmitting a light through a diastolic image radiograph 213 and a diastolic mask 218 to a mirror 214 coupled to a mirror 215 from which the image is projected to an eye 216 of an observer outside the box. Light is transmitted from the light source 212 through a systolic image radiograph and a systolic mask 218 to a mirror 219 coupled to a mirror 220, which transmits the systolic image through the half reflecting mirror 215 to the eye 216 of the observer outside the box.

Here again the masks are precisely out of phase, as shown, so that the systolic and diastolic images appear in an interlaced pattern to the observer, in accordance with the instant invention.

DESCRIPTION AND OPERATION OF THE CONVERTER IN FIG. 16

Referring now to FIG. 16 there is here illustrated a schematic block diagram of a data processing system for converting X-radiation images into electrical signals which are stored as inchoate diastolic and systolic images in a computer memory. The outputs of the memories are coupled to a data processor which is in turn coupled to a video display.

Thus an X-ray apparatus 225 transmits X-rays indicated at 226 through a patient 227 to an X-ray photoelectric converter 228. The converter 228 is coupled along a diastolic conductor to a diastolic storage portion 229 of an inchoate images storage unit generally indicated at 230. Another output of the converter 228 couples systolic signals to a systolic storage portion 231 of the storage unit 230. The diastolic storage is coupled to a data processor 232, the output of which is coupled to a video display circuit 233. A synchronizer 234 is coupled to the converter 228 and the X-ray apparatus 225. The synchronizer is also coupled to the patient 227, as shown.

The synchronizer, in response to the ECG signal from the patient, controls the X-ray apparatus as described above to synchronize the exposures with systole and diastole. During systole the converter produces electrical signals representative of the diastolic image, which are coupled to the diastolic storage unit 229 and stored. During systole the converter 228 couples the systolic image signals to the systolic storage unit 231. The data processor 232 derives the diastolic signals from the diastolic storage unit 229 and the systolic unit 231 to control the video display 233 to provide the systolic and diastolic images in an interlaced pattern in accordance with the invention.

Apparently Continuous Images—FIGS. 17(a) and 17(b)

It is sometimes desirable, particularly with respect to organ wall outlines, to present both images as appearing substantially continuous. In the case of a mask of the type described and illustrated with reference to FIGS. 5(a) and 5(b), the bars and slits must be sufficiently narrow that image outlines appear to be continuous. It is to be noted, however, that irrespective of how narrow the image elements may be, they are indeed finite and are therefore identifiable.

Referring now to FIG. 17(a) there is here illustrated an outline drawing of a radiograph 260 of the left ventricle 261 of the heart. The inner outline of the left ventricle is shown at end systole as indicated by the reference letter S. The ventricle 261 is illustrated at end diastole by the outer outline referenced D. Note that both outlines appear continuous. A circular portion 262 is shown substantially enlarged in FIG. 17(b). From FIG. 17(b) it is apparent that the systolic outline S occurs in image elements of finite width corresponding with the systolic image. Every other systolic area segments of the radiograph is indexed with an S, as shown. The diastolic image elements appear in the remaining bands, as shown. Under enlargement the image elements are interdigitally juxtaposed. The displacement between any part of such juxtaposed elements is, then, readily apparent.

DESCRIPTION AND OPERATION OF THE INVENTION IN THREE DIMENSIONS

A modification of well-known tomographic techniques as applied to nuclear cardiac scanning is used herein in accordance with this invention for isometrically projecting a three dimensional image. Here the patient receives internally a radioactive tracer, such as thallium$^{201}$ chloride, which lodges in the myocardium, or heart muscle and radiates to a nuclear camera.

A synchronizer, as described in the '360 patent referenced above, is coupled to the patient and a computer with systolic and diastolic memories. The synchronizer control repetitive imaging at end diastole and end systole to store inchoate D and S images in the computer memories. The images processed to provide S and D boroidal images elements which are coupled to output S and D memories, respectively. The output memories coupled to a display processor to control the presentation of a composite image on a cathode ray tube. A display control console is coupled to a switching circuit and display processor for alternately interlacing D and S image elements for isometric or planar sectional projection. A tomographic system which may readily be modified for use herein is described and illustrated in an article by Vogel et al entitled "New Method of Multiplanar Emission Tomography Using a Seven Pinhole Collimator and an Auger Scintillation Camera" (Jour. Soc. of Nuclear Medicine, 19, 6, 648–654, June 1978) and is hereby incorporated herein as an integral part of this specification and disclosure.

The system of Vogel as used in nuclear scan cardiology maps in three dimensions the distribution of thallium$^{201}$ in the myocardium of, e.g., the left ventricle.

The tomographic system of Vogel et al used in nuclear medicine to map in three dimensions the distribution of thallium$^{201}$ in the human myocardium in vivo is ideally suited to demonstrate a three-dimensional embodiment of the interlaced gated system.

Referring now to FIG. 18 there is here illustrated a schematic block diagram of a tomographic system embodying the invention. The system includes a gamma camera 240 equipped with a special, 7-pinhole collimator, which derives information about the spatial distribution of radioactive 201 Tl on the patient to a computer 242. The computer is programmed to accept seven images of the LV at end D and end S, store them, and compute the distribution of 201 Tl in seven discrete image elements in toroidal slices of the left-centricular myocardium. By imaging from the 50° left-anterior oblique projection, the slices are taken normal to the long axis of the left ventricle.

A physiological synchronizer 252, as described in the '360 patent referenced above, is coupled to the patient 240 and to the computer 242. The synchronizer 252 receives a QRS complex signal from the patient along conductors 243 and, after computing the times of occurrence of the extreme of the heart cycle, transmits D and S timing pulses along conductors 244 to the computer to control a switching circuit 245 for directing S and D image data from the camera 241 to S and D memories 246 and 247, respectively. Once the scan is completed, the computer 241 processes the contents of each memory 246 and 247, e.g., in accordance with algorithms described in the cited Vogel article. The output of the computer 241 is coupled to S and D output memories 248 and 249, respectively.

Each output memory contains inchoate toroidal image elements or slices of the myocardium corresponding to the S and D image elements. The image elements are coupled through another switching circuit 211 to a display processor 250 and intermixed as selected for a cathode ray tube 251. A display control console 210, coupled to the switch 211 and processor 250, enables the selection of the form of display. An isometric projection, as shown in FIG. 19, may be rotated about an axis or sliced along any plane, as shown in FIG. 20, as controlled by the console 210. By this means, successive S and D toroidal slices may alternately be taken from each output memory 248 and 249 and coupled to a common imaging medium, the display tube 251. The discrete image elements are intermixed and produce the discrete D and S images simultaneously independently in an interstitial pattern as shown in FIG. 19 or interlaced as shown in FIG. 20.

A typical isometric presentation of the left ventricle is shown in FIG. 19, and one of its cross-sections is shown in FIG. 20. In FIG. 19 a fluorescent medium 253 displays the D toroidal slices 254 and S slices 255.

Relative wall displacements and variations in wall thickness is readily apparent to the cardiologist. The displacements between systole and diastole are shown by the dimensions a for D thickness, b for D and S inner wall outlines, c for S thickness, d for D and S outer wall outlines, e for S inner wall diameter, f for D inner wall diameter, g for S outer wall diameter and h for D outer wall diameter.

Stepped Slit Mask—FIGS. 21 and 22

Instead of the mask in FIG. 5, a stepping mask may be used to expose a step at a time. Effectively with a single slit, one image element wide, say 3 millimeters, over a number of cardiac cycles, every other step is end D and each alternate, juxtaposed step is end S, to cover the entire area of presentation. For an area 300 mm long, 100 steps would be necessary. Assuming two steps per cardiac cycle, an entire exposure would require 50 cycles or from 20 to 100 seconds, depending upon heart rate.

By using multiple slits of width m spaced 2 Km apart, where K is an integer, the exposure time can be reduced accordingly. If K=1, the mask of FIG. 5 is reproduced.

If K is 10, 10 cardiac cycles are required. The exposure is then reduced by a factor of 5 or 4 to 20 seconds.

If more than two samples per cycle are required for 6 mm area segment width per cycle, the slit width is reduced proportionately. For three samples per cycle, the slit width is 2 mm and requires three steps per cycle for the exposure. Note, however, that the exposure is independent of the slit width. If 50 millisecond exposures are required for an adequate image, then for a cardiac cycle of 1000 milliseconds, 20 exposures may be taken in successive steps. For the 6 mm segment, the slit width becomes 300 microns and requires 20 steps. The slit width may, of course, be further reduced, e.g., to 100 microns, thereby requiring three cardiac cycles to complete the exposure. This has the effect of apparently increasing the number of steps to thirty per cycle to present an interlaced image closely resembling a continuously moving 100 micron slit. Each image element, however, is synchronized with cardiac pulsations and, therefore, can be indexed to correlate, e.g., with an ECG signal or QRS complex. Here the serrations of organ outlines would be smaller per pair of juxtaposed elements, tending to degrade the ease of diagnosis derived from relative displacements between the extreme of cardiac motion.

Referring then to FIGS. 21 and 22, there is here illustrated a mask operated by a stepping motor to implement the modes of operation discussed above. The system of FIGS. 1 and 9 are readily modified to incorporate a stepping mask by a suitable interface with the synchronizer.

Here, in FIG. 21(a), schematically illustrated is a mask 270 having a single slit 271 formed therein. A stepped motor 272 is coupled to the mask 270 for moving the mask vertically in successive steps, or discrete lineal increments, synchronized with cardiac motion. The motor receives step commands from a modification of the synchronizer in FIG. 6. An end view of the mask 270, in section, is shown in FIG. 21(b).

Referring to FIG. 22(a) a mask 275 is shown with a plurality slits 276 formed therein. The mask 275 is mechanically coupled to a stepping motor 277. An end view of the mask 275, in section, is shown in FIG. 22(b).

While there has hereinbefore been described what are now considered to be embodiments of the invention, it will be apparent that many modifications and changes will be made, thereto, without departing from the true scope of the invention. All such changes and modifications, therefore, are deemed to be a part of this invention.

What is claimed is:

1. X-ray apparatus for producing discrete images of a human organ in fluctuating motion, each said image being derived at a selected time related to systole and diastole, respectively, for simultaneous, independent presentation of said images on respective discrete areas within a common image plane, comprising:
   (A) means for X-irradiating said organ;
   (B) means for producing a diastolic timing signal for controlling the period of transmission of said X-radiation through said organ during diastole;
   (C) means for producing a systolic timing signal for controlling the period of transmission of said X-radiation through said organ during systole;
   (D) means for directing X-rays from said organ, during one said period, to selected discrete area segments of said image plane, each said segment corresponding with one discrete image element of one said discrete image;
   (E) means for directing X-rays from said organ, during the other said period, to selected discrete area segments of said image plane, each said segment corresponding with one discrete image element of the other said discrete image, said area segments and image elements being interdigital to produce said images in an interlaced pattern, such that relative displacements of said organ between systole and diastole may be simultaneously viewed and determined from juxtaposed said image elements; and
   (F) means enabling said systolic and diastolic images to be distinguished from, and identified relative to, each other.

2. The apparatus of claim 1 wherein:
said directing means includes a masking frame having alternate parallel slits and bars of equal intervals for exposing substantially half the area of an X-ray sensitive film in alternate equally spaced strips; and
means responsive to one said timing signal are included for repositioning said frame relative to said film such that the bars cover the sensitized areas of said film and expose substantially the remaining half of said film to produce said interlaced images for simultaneous presentation.

3. The apparatus of claim 2, wherein:
said bars are so shaped and formed of a material such that uncollimated X-rays are absorbed.

4. The apparatus of claim 2, wherein:
said one said timing signal is said diastolic timing signal.

5. The apparatus of claim 2, wherein:
said masking frame is interposed between said X-irradiation means and said organ.

6. The apparatus of claim 5, wherein said directing means further includes another such masking frame interposed between said organ and said image plane.

7. The apparatus of claim 2, wherein:
said masking frame is interposed between said organ and said image plane.

8. The apparatus of claim 2, wherein:
said frame moves and said film is fixed in position, whereby said images are formed from neighboring regions of said organ during systole and diastole, respectively.

9. The apparatus of claim 2, wherein:
said film moves and said frame is fixed in position, whereby said images are formed from the same regions of said organ during systole and diastole, respectively.

10. The apparatus of claim 2, wherein:
said slits are sufficiently narrow that each said image appears substantially continuous.

11. The apparatus of claim 10, wherein:
said slits are no greater than 1.0 millimeters wide.

12. The apparatus of claim 2, wherein:
said frame is normally upward in position for diastole; and
means are included to reposition said frame downwardly a distance of one slit width for systole.

13. The apparatus of claim 1 wherein:
said transmission periods coincide with minimum motion of said organ during systole and diastole, respectively.

14. The apparatus of claim 1, wherein:
said images are produced within one cardiac cycle.

15. The apparatus of claim 1, wherein:
said images are produced repetitively over a plurality of cardiac cycles.

16. The apparatus of claim 1, wherein:
said directing means includes means to limit said irradiation to selected regions of said organ.

17. The apparatus of claim 16, wherein:
said directing means includes means interposed between the source of said X-radiation and said organ to limit radiation from said organ to said selected areas of said image plane.

18. The apparatus of claim 1, wherein:
said directing means includes means interposed between said organ and said image plane to limit radiation from said organ to said selected areas of said image plane.

19. The apparatus of claim 1, wherein said apparatus includes:
means for producing a signal representative of one said period;
means for storing said representative signal; and
means for controlling the other said transmission period in accordance with said stored signal to normalize the exposures of said images in a predetermined manner.

20. The apparatus of claim 19, wherein said apparatus includes:
means for counting X-ray photons during one said transmission period;
means for storing said photon count; and
means for controlling the other said transmission period in accordance with said photon count, thereby substantially to equalize the image radiation exposures.

21. The apparatus of claim 20, wherein:
means are provided for controlling the elapsed time of said other transmission period in accordance with the elapsed time of said photon count.

22. The apparatus of claim 20, wherein:
means are provided to control the photon count during said other transmission period to be substantially equal to the first said photon count.

23. The apparatus of claim 22, wherein:
said photon counting means is directly responsive to said X-irradiation means.

24. The apparatus of claim 23, wherein:
said photon counting means includes means directly responsive to X-ray photons from said organ.

25. The apparatus of claim 1, wherein:
said discrete area segments and image elements are sufficiently narrow that each said image appears substantially continuous.

26. The apparatus of claim 1, wherein said pparatus includes:
means for converting X-ray photons at said image plane into electrical signals representative of each said image.

27. The pparatus of claim 26, wherein said apparatus includes:
fluorescent means for simultaneously displaying said images in response to said electrical signals.

28. The apparatus of claim 26, wherein:
means are provided for processing said electrical signals relative to corresponding selected points of said organ; and
means are further provided for displaying said images with respect to said selected points.

29. The apparatus of claim 1, wherein said apparatus includes:
fluorescent means for simultaneously displaying said images.

30. X-ray apparatus for deriving an electrocardiographic signal from a human for producing discrete images of a human organ in fluctuating motion, each said image being composed of a set of discrete image elements and derived at a selected time related to the cardiac cycle, for simultaneous, independent presentation of said images on respective discrete areas within a common image plane, each said area having a set of discrete area segments, each of which corresponds with one said image element, comprising:

(A) means for X-irradiating said human organ;
(B) means for deriving an electrocardiographic signal, indicative of the cardiac cycle, from said human;
(C) means for deriving a first timing signal for controlling said X-radiation from said organ to said image plane for a first period;
(D) means for deriving a second timing signal, separated from said first timing signal by a discrete time interval, for controlling said X-radiation from said organ to said image plane during a second period;
(E) means for directing the first said X-radiation, during said first period, to selected said discrete area segments of said image plane corresponding with said discrete elements of one said discrete image;
(F) means for directing the second said X-radiation, during the other said period, to selected said discrete area segments of said image plane corresponding with said discrete elements of the other said discrete image, said corresponding elements and area segments being interdigitally juxtaposed to produce said images in an interlaced pattern, such that a relative change of condition of said organ during said interval can be determined from juxtaposed said image elements; and
(G) means enabling said discrete images to be distinguished from, and identified relative to, each other.

31. The X-ray apparatus of claim 30, wherein:
said directing means includes masking means positioned between the source of said X-radiation and said human.

32. The X-ray apparatus of claim 31, wherein:
another said masking means is positioned between said human and said image plane.

33. The X-ray apparatus of claim 30, wherein:
said directing means includes masking means positioned between said human and said image plane.

34. The X-ray apparatus of claim 30, wherein:
said directing means includes a masking frame having alternate parallel slits and bars of equal intervals for exposing substantially half the area of presentation of an X-radiographic film in alternate equally spaced bands.

35. The X-ray apparatus of claim 34, wherein:
said frame is normally positioned for one said discrete image; and
means responsive to one said timing signal are included for repositioning said frame relative to said film such that the bars cover the sensitized areas of said film and expose substantially the remaining half of the area of presentation of said film to produce said interlaced images for simultaneous presentation.

36. The X-ray apparatus of claim 30, wherein: said timing signals occur within one cardiac cycle.

37. X-ray apparatus of claim 30, wherein: said fluctuating motion is recurrent and said image plane receives X-radiation over a plurality of successive cardiac cycles.

38. The X-ray apparatus of claim 37, wherein:
said directing means includes masking means having an exposure slit means; and
means for discretely positioning said slit means in accordance with said timing signals.

39. The X-ray apparatus of claim 30, wherein:
said directing means include a masking means having alternate parallel slits and bars of equal widths for controlling the exposure of an X-radiographic film such that said film is exposed only during said periods.

40. The X-ray apparatus of claim 30, wherein:
said directing means include a masking means having exposure slit means; and
means for discretely positioning said slit means in accordance with said timing signals.

* * * * *